US011802310B2

(12) United States Patent
Komata et al.

(10) Patent No.: US 11,802,310 B2
(45) Date of Patent: Oct. 31, 2023

(54) METHOD FOR EVALUATING PHYSICAL CONDITIONS, METHOD FOR PRESENTING INFORMATION, AND METHOD FOR SCREENING FOR SUBSTANCE CAPABLE OF IMPROVING OR PREVENTING PHYSICAL CONDITIONS

(71) Applicants: TAK-CIRCULATOR CO., LTD, Tokyo (JP); THE UNIVERSITY OF TOKYO, Tokyo (JP)

(72) Inventors: Makiko Komata, Tokyo (JP); Kouta Tachibana, Tokyo (JP); Katsuhiko Shirahige, Tokyo (JP); Takashi Sutani, Tokyo (JP)

(73) Assignees: MYSKIN CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 1397 days.

(21) Appl. No.: 15/745,468

(22) PCT Filed: Jul. 21, 2016

(86) PCT No.: PCT/JP2016/071355
§ 371 (c)(1),
(2) Date: Jan. 17, 2018

(87) PCT Pub. No.: WO2017/014256
PCT Pub. Date: Jan. 26, 2017

(65) Prior Publication Data
US 2018/0208982 A1    Jul. 26, 2018

(30) Foreign Application Priority Data

Jul. 21, 2015  (JP) ................................. 2015-143583
May 19, 2016  (JP) ................................. 2016-100475

(51) Int. Cl.
| | | |
|---|---|---|
| *C12Q 1/6869* | (2018.01) | |
| *G16B 20/00* | (2019.01) | |
| *G16B 40/00* | (2019.01) | |
| *C12Q 1/68* | (2018.01) | |
| *C12N 15/09* | (2006.01) | |
| *G01N 33/569* | (2006.01) | |
| *G16B 40/30* | (2019.01) | |
| *G16B 20/20* | (2019.01) | |

(52) U.S. Cl.
CPC .......... *C12Q 1/6869* (2013.01); *C12N 15/09* (2013.01); *C12Q 1/68* (2013.01); *G01N 33/56911* (2013.01); *G16B 20/00* (2019.02); *G16B 20/20* (2019.02); *G16B 40/00* (2019.02); *G16B 40/30* (2019.02); *G01N 2570/00* (2013.01); *G01N 2800/20* (2013.01)

(58) Field of Classification Search
CPC ........ C12Q 1/6869; C12Q 1/68; G16B 20/20; G16B 40/00; G16B 40/30; G16B 20/00; C12N 15/09; G01N 33/56911
See application file for complete search history.

(56) References Cited

FOREIGN PATENT DOCUMENTS

| | | |
|---|---|---|
| JP | 2007039423 A | 2/2007 |
| JP | 2013 188 326 | 9/2013 |
| JP | 2015 512 255 | 4/2015 |
| WO | 2013 142 378 | 9/2013 |
| WO | 2014 023 803 | 2/2014 |
| WO | 2014 205 088 | 12/2014 |

OTHER PUBLICATIONS

A-1(A). World Fusion Co., Ltd, "*Skin Flora: Beautiful Skin by Indigenous Bacteria Check*", Dec. 1, 2015 (year/month/day), Internet <URL: https://www.s-kin.jp/>.
B-1(B). World Fusion Co., Ltd., "*Skin Flora: Beautiful Skin by Indigenous Bacteria Check | Utilization Flow of Skin Check*", Dec. 1, 2015 (year/month/day), internet <URL:https://www.s-kin.jp/blank-9>.
C-1(C). World Fusion Co., Ltd., "*Skin Flora: Beautiful Skin by Indigenous Bacteria Check | What is Understood from Test Results*", Dec. 1, 2015 (year/month/day), Internet <URL: https://www.s-kin.jp/blank-12>.
D-1(D). World Fusion Co., Ltd., "*Skin Flora: Beautiful Skin by Indigenous Bacteria Check | Recommended Cosmetics from Skin Flora*", Dec. 1, 2015 (year/month/day), Internet <URL: https://www.s-kin.jp/blank-6>.
E-1(E). World Fusion Co., Ltd., "*Skin Bacterial Flom Analysis*", Dec. 1, 2015(year/month/day), internet <URL: https://www.s-kin.jp/blank-1>.
F-1(F). World Fusion Co., Ltd., "*Skin Bacterial Flora Analysis*" Dec. 1, 2015(year/month/day), Internet <URL: https://www.s-kin.jp/blank-4>.
G-1(G). World Fusion Co., Ltd., "*Skin Flora: Beautiful Skin Check by Indigenous Bacteria | News*", Dec. 1, 2015 (year/month/day), Internet <URL: https://www.s-kin.jp/blank-3>.
H-1(H). World Fusion Co., Ltd., "*Skin Flora: Beautiful Skin. Check by Indigenous Bacteria | From Estimate to Delivery*", Dec. 1, 2015 (year/month/day), internet <URL: https://www.s-kin.jp/blank-8>.

(Continued)

*Primary Examiner* — Jerry Lin
(74) *Attorney, Agent, or Firm* — Emerson Thomson Bennett; Daniel A. Thomson

(57) ABSTRACT

The purpose of the present invention is to provide: a method for evaluating various physical conditions accurately; a method for presenting information utilizing the aforementioned method; and a method of screening for a substance capable of improving or preventing physical conditions. A method for evaluating a physical condition of a subject comprises the steps of: determining the value of an abundance of a skin flora, which is collected from the surface of the skin of the subject, on the surface of the skin or the value of a parameter calculated on the basis of the abundance, wherein the reference values for the correlation between the abundance or the parameter with the physical condition has been produced; and then comparing the value with the reference values.

31 Claims, 12 Drawing Sheets

(56) References Cited

OTHER PUBLICATIONS

I-1(I). World Fusion Co., Ltd., "*Skin Bacteria Flora Analysis*", Dec. 1, 2015 (year/month/day), Internet <URL: https://www.s-kin.jp/260526>.
3. Tokyo ISEA Clinic/Medical Corp., 12th Meeting [World First] Opening of Skin Indigenous Bacteria Examination "*Beautiful Skin Bacteria Docks*", May 18, 2015 (year/month/day), internet <URL: https://prtimes.jp/a/?c=4342&r=51&f=d4342-20150516-5261.pdf.
Dietert, et al., *The microbiome and sustainable healthcare*, Healthcare, Mar. 2015, vol. 3, p. 100-129.
5. Maruzen Co., Ltd. "*Encyclopedia of Cosmetics*" (2003) pp. 628-631.
Reasons for Refusal issued to JP Patent Application No. 2016-100475, dated Jul. 19, 2016.
28 Notice of Reasons for revocation of a patent issued to JP Patent No. 6046849, dated Dec. 1, 2017.
8. Kasa, "*Research Concerning Generation Mechanism of Ultraviolet Skin Damage by Singlet Oxygen*" Mar. 27, 2015 (year/month/day), internet <http://gazo.dl.itc.u-tokyo.ac.jp/gakui/data/h21/217322/217322a.pdf>.
Schloss, An integrated view of the skin microbiome, Nature, 2014, vol. 514, p. 44-45.
7. *Scientific Reports* (Jul. 16, 2015) 5:11845 DOI:10.1038/srep11845.
6. Shindan To Chiryo K.K., "*Simple Statistics Introduction for Medical Treatment Systems*" (2009) pp. 70 to 87.
9. Yakugaku Zasshi (2012) vol. 3, pp. 261 to 269.
Zhang, et al., Characterization of the skin fungal microbiota in patients with atopic dermatitis and in healthy subjects. Microbiology and Immunology, 2011, vol. 55, p. 625-632.

Redel, et al., "Quantitation and Composition of Cutaneous Microbiote in Diabetic and Nondiabetic Men," Cutaneous Microbiome of Diabetic Men, JID, 2013:207, Jan. 8, 2018, 1105-1114.
EPO, "European Search Report," EP Patent Appln, No. EP 168 278 16.6, dated Dec. 5, 2018.
Shuwa System Co., Ltd, "Medical statistics known gently in the world" (2011), p. 146-150 As the English translation of this document is not available, we submit the machine translation of the Office Action JP6874244 as a concise explanation of the relevance.
Maruzen Co., Ltd. "Cosmetics encyclopedia", (2003), p. 591 As the English translation of this document is not available, we submit the machine translation of the Office Action JP6874244 as a concise explanation of the relevance.
Notice of Reasons for Revocation issued in the JP Patent Application No. JP Patent No. 6874244, dated Mar. 8, 2022.
Applicant, Translation of Relevant Portions of Documents in Notice of reasons for revocation of a patent issued to JP Patent No. 6046849, dated Dec. 1, 2017, prepared on Feb. 5, 2018.
Yuko Kozono, "Concerning the URL of Exhibit 4", Jul. 26, 2017.
World Fusion Co., Ltd., Document distributed in the "12th Class A Data Analysis Seminar", Sep. 8, 2015.
World Fusion Co., Ltd., Evidence of "12th Class A Data Analysis Seminar", Jul. 20, 2017.
World Fusion Co., Ltd., "Evidence", Jun. 14, 2017.
World Fusion Co., Ltd., Evidence of the presentation document "Relation Between Skin Bacterial Flora of Japanese People and Skin Condition", Jul. 20, 2017.
NIH Human Microbiome Project defines normal bacterial makeup of the body, NIH press release [online], 2012, search date: Jul. 15, 2016, Internet <URL:https://www.genome.gov/27549144>.
World Fusion Co., Ltd., Reception roster of participants of "12th Class A Data Analysis Seminar", Sep. 8, 2015.
World Fusion Co., Ltd., "Relation Between Skin Bacterial Flora of Japanese People and Skin Condition", presentation document, Sep. 8, 2015.

FIG. 16

| PHYSICAL SYMPTOMS FOUND TO SHOW CORRELATION | BACTERIAL SPECIES SHOWING CORRELATION | AMOUNT OF BACTERIUM | | ACTUAL AGE | |
|---|---|---|---|---|---|
| | | COEFFICIENT OF CORRELATION | p_VALUE | COEFFICIENT OF CORRELATION | p_VALUE |
| SKIN TYPE [DRYNESS(0)<->OILINESS(2)] | k__Bacteria;p__Actinobacteria;c__Actinobacteria;o__Actinomycetales;f__Propionibacteriaceae;g__Propionibacterium;s__acnes | 0.233492208 | 1.54E-13 | -0.015189154 | 0.867919181 |
| | k__Bacteria;p__Proteobacteria;c__Gammaproteobacteria;o__Xanthomonadales;f__Xanthomonadaceae;g__;s__ | -0.169264987 | 5.52E-08 | -0.038688578 | 0.233300571 |
| | k__Bacteria;p__Proteobacteria;c__Alphaproteobacteria;o__Sphingomonadales;f__Sphingomonadaceae;g__Sphingomonas;s__ | -0.139864984 | 4.84E-06 | -0.058828367 | 0.0543562 |
| | k__Bacteria;p__Proteobacteria;c__Gammaproteobacteria;o__Vibrionales;f__Pseudoalteromonadaceae;g__Pseudoalteromonas;s__porphyrae | -0.137673286 | 1.11E-05 | -0.042665831 | 0.171381685 |
| | k__Bacteria;p__Proteobacteria;c__Gammaproteobacteria;o__Vibrionales;f__Vibrionaceae;g__Vibrio;Other | -0.137089648 | 1.15E-05 | -0.043998579 | 0.15749427 |
| | k__Bacteria;p__Proteobacteria;c__Gammaproteobacteria;o__Aeromonadales;f__Aeromonadaceae;Other;Other | -0.135780237 | 1.29E-05 | -0.046920721 | 0.133546027 |
| | k__Bacteria;p__Proteobacteria;c__Gammaproteobacteria;o__Vibrionales;f__Pseudoalteromonadaceae;g__Pseudoalteromonas;Other | -0.132439472 | 2.10E-05 | -0.0473192 | 0.127136194 |
| | k__Bacteria;p__Proteobacteria;c__Gammaproteobacteria;Other;Other;Other | -0.124925554 | 7.30E-05 | -0.043847362 | 0.164448627 |
| | k__Bacteria;p__Firmicutes;c__Bacilli;o__Lactobacillales;f__Streptococcaceae;g__Streptococcus;s__ | -0.117342888 | 0.000125912 | -0.062634149 | 0.040200502 |
| | k__Bacteria;p__Firmicutes;c__Bacilli;o__Gemellales;f__Gemellaceae;g__;s__ | -0.115942993 | 0.000187823 | -0.073477098 | 0.015455873 |
| | k__Bacteria;p__Proteobacteria;c__Alphaproteobacteria;o__Rhodospirillales;f__Acetobacteraceae;g__Roseomonas;s__mucosa | -0.113511486 | 0.000191766 | -0.070326809 | 0.020600854 |
| | k__Bacteria;p__Proteobacteria;c__Alphaproteobacteria;o__Rhodospirillales;f__Acetobacteraceae;g__Acidocella;s__ | -0.112633444 | 0.000212478 | -0.080809036 | 0.007783268 |
| | k__Bacteria;p__Firmicutes;c__Bacilli;o__Bacillales;f__Planococcaceae;g__;s__ | -0.111694096 | 0.000240189 | -0.080867716 | 0.007746735 |
| | k__Bacteria;p__Proteobacteria;c__Betaproteobacteria;o__Burkholderiales;f__Burkholderiaceae;g__Lautropia;s__ | -0.109397017 | 0.000385918 | -0.056349401 | 0.06790678 |
| | k__Bacteria;p__Proteobacteria;c__Gammaproteobacteria;o__Alteromonadales;f__Shewanellaceae;g__Shewanella;s__ | -0.109334799 | 0.000414239 | -0.055856376 | 0.070652413 |
| | k__Bacteria;p__Firmicutes;c__Bacilli;o__Lactobacillales;f__Carnobacteriaceae;g__Granulicatella;s__ | -0.108255695 | 0.000476529 | -0.073561835 | 0.015424588 |
| FRECKLES | k__Bacteria;p__Actinobacteria;c__Actinobacteria;o__Actinomycetales;f__Corynebacteriaceae;g__Corynebacterium;s__kroppenstedtii | 0.106836433 | 0.000045559 | -0.070368789 | 0.020736686 |
| CONSPICUOUS PORES DUE TO SAGGING | k__Bacteria;p__Actinobacteria;c__Actinobacteria;o__Actinomycetales;f__Propionibacteriaceae;g__Propionibacterium;s__acnes | 0.114583509 | 0.000315596 | 0.150297673 | 2.42E-06 |
| PIMPLES | k__Bacteria;p__Actinobacteria;c__Actinobacteria;o__Actinomycetales;f__Propionibacteriaceae;g__Propionibacterium;s__acnes | 0.099188127 | 0.000348171 | -0.501038374 | 9.93E-67 |
| UNSMOOTHED/UNUNIFORMED SKIN TEXTURE | k__Bacteria;p__Actinobacteria;c__Actinobacteria;o__Actinomycetales;f__Propionibacteriaceae;g__Propionibacterium;s__acnes | 0.115090532 | 0.000321844 | -0.007268341 | 0.819729297 |
| | k__Bacteria;p__Actinobacteria;c__Actinobacteria;o__Actinomycetales;f__Propionibacteriaceae;g__Propionibacterium;s__granulosum | 0.108102548 | 0.000415429 | -0.053594196 | 0.0794367322 |
| YELLOWISH SKIN | k__Bacteria;p__Firmicutes;c__Bacilli;o__Bacillales;f__Bacillaceae;g__Bacillus;s__ | 0.138553876 | 1.92E-07 | 0.004045565 | 0.893633804 |
| | k__Bacteria;p__Actinobacteria;c__Actinobacteria;o__Actinomycetales;f__Micrococcaceae;g__Rothia;s__dentocariosa | 0.146585451 | 1.71E-06 | -0.012832496 | 0.9259232995 |
| | k__Bacteria;p__Actinobacteria;c__Actinobacteria;o__Actinomycetales;f__Actinomycetaceae;g__Actinomyces;s__ | 0.120954336 | 0.000249702 | 0.004421669 | 0.8347885596 |
| | k__Bacteria;p__Actinobacteria;c__Actinobacteria;o__Actinomycetales;f__Micrococcaceae;g__Rothia;Other | 0.10989264 | 0.000363198 | 0.013901562 | 0.647417479 |
| DRY/FLAKING SKIN | k__Bacteria;p__Actinobacteria;c__Actinobacteria;o__Actinomycetales;f__Propionibacteriaceae;g__Propionibacterium;s__acnes | -0.107193452 | 0.000561242 | -0.275512008 | 2.48E-18 |
| OILY/SHINY SKIN | k__Bacteria;p__Actinobacteria;c__Actinobacteria;o__Actinomycetales;f__Propionibacteriaceae;g__Propionibacterium;s__acnes | 0.160068127 | 5.54E-08 | -0.314360141 | 1.26E-23 |
| | k__Bacteria;p__Proteobacteria;c__Gammaproteobacteria;o__Xanthomonadales;f__Xanthomonadaceae;g__;s__ | -0.102181109 | 0.000412882 | -0.359314113 | 2.78E-33 |
| | k__Bacteria;p__Firmicutes;c__Bacilli;o__Lactobacillales;f__Streptococcaceae;g__Streptococcus;s__ | -0.098331428 | 0.000527308 | -0.371601277 | 1.13E-36 |
| EXPANDED/SEBUM-FILLED PORES | k__Bacteria;p__Actinobacteria;c__Actinobacteria;o__Actinomycetales;f__Propionibacteriaceae;g__Propionibacterium;s__acnes | 0.195832742 | 5.93E-11 | -0.281748014 | 1.07E-20 |
| | k__Bacteria;p__Proteobacteria;c__Gammaproteobacteria;o__Xanthomonadales;f__Xanthomonadaceae;g__;s__ | -0.13638832 | 3.55E-06 | -0.309582798 | 6.05E-25 |
| | k__Bacteria;p__Proteobacteria;c__Gammaproteobacteria;o__Vibrionales;f__Pseudoalteromonadaceae;g__Pseudoalteromonas;Other | -0.122023534 | 3.22E-05 | -0.314597219 | 1.00E-25 |
| | k__Bacteria;p__Proteobacteria;c__Gammaproteobacteria;o__Alteromonadales;f__Shewanellaceae;g__Shewanella;s__ | -0.117430149 | 5.66E-05 | -0.319284998 | 1.05E-26 |
| | k__Bacteria;p__Firmicutes;c__Bacilli;o__Lactobacillales;f__Streptococcaceae;g__Streptococcus;s__ | -0.113036889 | 8.55E-05 | -0.328036951 | 1.44E-28 |
| | k__Bacteria;p__Proteobacteria;c__Gammaproteobacteria;o__Vibrionales;f__Pseudoalteromonadaceae;g__Pseudoalteromonas;s__porphyrae | -0.112784648 | 0.000135677 | -0.313782774 | 2.89E-25 |
| | k__Bacteria;p__Proteobacteria;c__Alphaproteobacteria;o__Sphingomonadales;f__Sphingomonadaceae;g__Novosphingobium;s__ | -0.106549109 | 0.000251906 | -0.322754855 | 2.77E-27 |
| | k__Bacteria;p__Proteobacteria;c__Gammaproteobacteria;o__Vibrionales;f__Vibrionaceae;g__Vibrio;Other | -0.108098106 | 0.000322745 | -0.316350488 | 1.06E-25 |
| | k__Bacteria;p__Betaproteobacteria;o__Burkholderiales;f__Burkholderiaceae;g__Lautropia;s__ | -0.104578336 | 0.000334633 | -0.322284923 | 3.96E-27 |
| DECREASED LIVER FUNCTION (BLOOD TEST VALUE) | k__Bacteria;p__Proteobacteria;c__Epsilonproteobacteria;o__Campylobacterales;f__Campylobacteraceae;g__Campylobacter;s__ | 0.127295146 | 3.17E-05 | 0.026598503 | 0.382746867 |
| | k__Bacteria;p__Firmicutes;c__Bacilli;o__Bacillales;f__Bacillaceae;g__Bacillus;s__ | 0.126675042 | 3.28E-05 | 0.03120288 | 0.304355853 |
| | k__Bacteria;p__Firmicutes;c__Bacilli;o__Lactobacillales;f__Streptococcaceae;g__Streptococcus;s__anginosus | 0.107955988 | 0.000471855 | 0.011959938 | 0.294184639 |
| HIGH URIC ACID VALUE (RELATIVELY HIGH) | k__Bacteria;p__Actinobacteria;c__Actinobacteria;o__Actinomycetales;f__Micrococcaceae;g__Rothia;Other | 0.290272391 | 2.18E-22 | 0.075806529 | 0.009456764 |
| | k__Bacteria;p__Actinobacteria;c__Actinobacteria;o__Actinomycetales;f__Brevibacteriaceae;g__Brevibacterium;s__ | 0.286642346 | 1.17E-21 | 0.050263888 | 0.086951 |
| | k__Bacteria;p__Actinobacteria;c__Actinobacteria;o__Actinomycetales;f__Sphingomonadales;f__Erythrobacteraceae;g__;s__ | 0.178386274 | 7.37E-09 | 0.042690386 | 0.161285307 |
| | k__Bacteria;p__Actinobacteria;c__Actinobacteria;o__Alphaproteobacteria;o__Rhodobacterales;f__Rhodobacteraceae;g__;s__ | 0.162271746 | 1.37E-07 | 0.046294661 | 0.114618227 |
| | k__Bacteria;p__Actinobacteria;c__Actinobacteria;o__Actinomycetales;f__Propionibacteriaceae;g__Propionibacterium;s__granulosum | 0.156815495 | 3.13E-07 | 0.061666935 | 0.04185752 |
| KNEE PAIN | k__Bacteria;p__Firmicutes;c__Clostridia;o__Clostridiales;f__[Tissierellaceae];g__WAL_1855D;s__ | 0.11757272 | 7.51E-05 | 0.210181531 | 1.67E-14 |
| | k__Bacteria;p__Firmicutes;c__Clostridia;o__Clostridiales;f__Veillonellaceae;g__Veillonella;s__parvula | 0.102798789 | 0.000588325 | 0.21418511 | 1.28E-12 |
| OSTEOPOROSIS | k__Bacteria;p__Proteobacteria;c__Gammaproteobacteria;o__Pseudomonadales;f__Pseudomonadaceae;g__Pseudomonas;s__ | 0.156611133 | 5.45E-08 | 0.12246772 | 8.96E-20 |
| | k__Bacteria;p__Proteobacteria;c__Alphaproteobacteria;o__Rhizobiales;f__Methylobacteriaceae;g__Methylobacterium;Other | 0.100913561 | 0.00044677 | 0.336011808 | 8.53E-30 |
| AUTONOMIC IMBALANCE | k__Bacteria;p__Proteobacteria;c__Betaproteobacteria;o__Burkholderiales;f__Oxalobacteraceae;g__;s__ | 0.11224025 | 0.000239508 | -0.050520886 | 0.0985314772 |
| DIABETES | k__Bacteria;p__Actinobacteria;c__Actinobacteria;o__Actinomycetales;Other;Other;Other | 0.140084529 | 2.06E-06 | 0.070290727 | 0.020018428 |
| THIN HAIR/HAIR LOSS | k__Bacteria;p__Actinobacteria;c__Actinobacteria;o__Actinomycetales;f__Microbacteriaceae;g__Microbacterium;Other | 0.121523575 | 5.47E-05 | 0.205247451 | 1.34E-11 |

METHOD FOR EVALUATING PHYSICAL CONDITIONS, METHOD FOR PRESENTING INFORMATION, AND METHOD FOR SCREENING FOR SUBSTANCE CAPABLE OF IMPROVING OR PREVENTING PHYSICAL CONDITIONS

TECHNICAL FIELD

The present invention relates to a method of evaluating a physical condition, a method of presenting a useful ingredient, and a method of screening for a substance which may improve or prevent a physical condition.

BACKGROUND ART

Conventionally, human skin conditions are evaluated using those indices such as resilience, texture, spots, wrinkles, the level of moisture, the level of oiliness, and the amount of moisture transpiration (barrier function). Methods of evaluating these indices include questionnaire studies, image analysis of the skin surface disclosed in Patent Document 1 and the like (for resilience, texture, spots, wrinkles, and the like), and instrumental measurements (for the level of moisture, the level of oiliness, the amount of moisture transpiration, and the like).

However, questionnaire studies may suffer from significant bias due to questionee's subjectivity, and tend to yield less objective evaluations. Unlike questionnaire studies, image analysis can provide objective indices. Nonetheless, accurate evaluation of skin conditions may still be difficult due to varied skin qualities depending on with/without face cleansing, foundation, skin cream, and the like.

Further, evidence has been accumulating which suggests that factors affecting skin conditions may not necessarily be limited to the aforementioned indices, and there exists a skin condition difficult to be evaluated by the conventional technologies which are dependent on the aforementioned indices. There are increasing demands for a technology allowing such a skin condition to be evaluated. In addition to such a skin condition, there also exist demands for a technology allowing a general physical condition to be evaluated.

Patent Document 1: Japanese Unexamined Patent Application, Publication No. 2013-188326

DISCLOSURE OF THE INVENTION

Problems to be Solved by the Invention

The present invention is made in view of the above traditional circumstances. An object of the present invention is to provide a method of evaluating a skin condition. The method can provide objective evaluation, and is less affected by varied skin qualities due to face cleansing and the like.

Another object of the present invention is to provide a method of accurately evaluating various physical conditions, a method of presenting information obtained from the above method, and a method of screening for a substance which may improve or prevent a physical condition.

Means for Solving the Problems

The human body comprises about 60 trillion cells while 100 trillion or more bacteria are thought to inhabit the surface and inside of the human body. These indigenous bacteria are increasingly considered to be profoundly involved in human health conditions and diseases. That is, the human body can be viewed as a symbiont of human cells and microbial floras (bacterial and fungal floras). The present inventors studied microbial floras inhabiting the faces of many human subjects, and then have arrived at an idea that a microbial flora on the skin surface of a human subject could be used as a novel index for a physical condition. After conducting extensive studies, the present inventors found that the abundance proportion of a specific indigenous bacterium present on the skin surface and the like can serve as a good index for a physical condition. Then the present invention has been completed.

(1) A method of evaluating a physical condition of a subject, the method including the step of: determining a value of an abundance proportion of a skin indigenous microorganism on a skin surface of the subject among a skin microbial flora collected from the skin surface or a parameter based on the abundance proportion, a correlation criterion of the abundance proportion or parameter with the physical condition being pre-established, and then comparing the value with the correlation criterion.

(2) A method of presenting information to a subject, the method including the steps of: evaluating a physical condition of the subject by the method according to (1), and presenting, when the physical condition is evaluated to be outside a target condition, information registered in a data base as an ingredient capable of directing the value of the abundance proportion or parameter toward a numerical range of an abundance proportion or parameter obtained based the correlation criterion when the physical condition is within the target condition.

(3) The method according to (2), further including the steps of: re-evaluating the physical condition of the subject by the method according to (1) after consumption of the ingredient, and updating the information based on the extent of improvement in the physical condition after the re-evaluation.

(4) A method of screening for a substance capable of improving or preventing a physical condition, the method including the step of: selecting a candidate substance based on how the candidate substance changes the value of an abundance proportion of a skin indigenous microorganism on a skin surface or a parameter based on the abundance proportion, a correlation criterion of the abundance proportion or parameter with the physical condition being pre-established.

(5) The method according to any one of (1) to (4), wherein the abundance proportion is an abundance proportion of at least one bacterium selected from the group consisting of bacteria belonging to phylum Actinobacteria, bacteria belonging to phylum Proteobacteria, and bacteria belonging to phylum Firmicutes.

(6) The method according to any one of (1) to (5), wherein the parameter is at least one selected from the group consisting of the ratio or difference of the abundance proportions and a diversity index of skin indigenous microorganisms.

(7) The method according to any one of (1) to (6), wherein the physical condition is at least one selected from the group consisting of skin age; oily skin; pimpled skin; and spots, dullness, sagging, wrinkles, resilience conditions, and pore conditions of the skin.

(8) The method according to any one of (1) to (6), wherein the physical condition is at least one of thin hair and hair loss.

(9) The method according to any one (1) to (6), wherein the physical condition is at least one of periodontal disease and alveolar pyorrhea.

(10) The method according to any one (1) to (6), wherein the physical condition is menopause.

(11) The method according to any one of (1) to (6), wherein the physical condition is at least one of liver function, high uric acid, knee pain, osteoporosis, autonomic imbalance, yellowish skin, and diabetes.

(12) The method according to any one of (1) to (11), wherein the correlation criterion is a correlation criterion between the physical condition and the abundance proportion or parameter after an effect from at least one phenomenon known to correlate with the physical condition is removed.

(13) The method according to any one (1) to (12), wherein the correlation criterion is created for a sub-population into which a population is categorized according to at least one selected from the group consisting of age, sex, residential area, nationality, and race.

A bacterial flora on a skin surface is preferably analyzed by analyzing DNA present on the skin surface. The method of investigating a bacterial flora based on DNA can yield results more accurately reflecting the bacterial flora as compared with the method of estimating a bacterial flora by culturing bacteria collected from a skin surface on an agar medium. This is because the percentage of microorganisms cultivable on an agar medium is thought to be only about 1%, and most microbial species are difficult to be cultured. In contrast, the method involving analysis of DNA enables a bacterial flora collected from a skin surface to be analyzed accurately and truly.

The analysis of a bacterial flora is preferably performed by a method including: a detachment step of detaching an adhesive member which has been contacted with a skin surface to allow bacteria present on the skin surface to adhere to the adhesive member, an extraction step of extracting DNA contained in the bacteria by allowing the adhesive member to which the bacteria has been adhered to make contact with a liquid, and a genome analysis step of performing genome analysis of the extracted DNA.

In the aforementioned method of analyzing a bacterial flora, the adhesive member is contacted with a skin surface, and then detached from the skin surface to collect bacteria present on the skin surface while the bacteria remain adhering to the adhesive member (the detachment step). Thereby, amongst the entire skin surface bacteria, those present on a skin surface with which the adhesive member makes contact can be allowed to adhere to and collected at a surface of the adhesive member while maintaining the original distribution. Advantageously, the aforementioned method can eliminate a risk of variations in the data of a bacterial flora due to varied swabbing force and varied swabbing area in the method of swabbing a skin surface with a swab. Further, the bacterial flora of a skin surface can be truly copied. Subsequently, the adhesive member having the bacteria adhered is allowed to make contact with a liquid to extract DNA included in bacteria (the extraction step). Therefore, a DNA solution, from which a bacterial flora can be determined, can be prepared very rapidly from the adhesive member having the bacteria adhered as compared with a method of sorting substances which have adhered to the surface of an adhesive member using a magnifying glass and the like to prepare a sample. This can minimize a change in the bacterial flora during the course of sample preparation. Then, the extracted DNA can be analyzed with the next-generation sequencer (NGS) and the like to simply and uniformly determine the bacterial flora present on the skin surface. Nonetheless, the means for collecting microorganisms from a skin surface is not be limited to an adhesive member, and a swab and others may be used. Further, there is also no particular limitation for the means for extracting DNA and the means for analyzing DNA.

Effects of the Invention

Results from analysis of bacterial floras by the present inventors show that the relative amount of a bacterium belonging to phylum Actinobacteria and the abundance ratio of a bacterium belonging to phylum Proteobacteria and a bacterium belonging to phylum Firmicutes, which are specific indigenous bacteria present on a facial skin surface, may be determined to evaluate various facial skin conditions such as pimples and expanded pores and susceptibility to various physical symptoms not localized to the face such as periodontal disease and thin hair/hair loss in the head.

Further, the present inventors also found that the relative amount of a bacterial species may correlate with susceptibility to other physical symptoms. For example, the followings and others were found to show a correlation with the relative amount of a bacterial species indicated in parentheses: high uric acid values (genus *Rothia*, genus *Brevibacterium*, family Erythrobacteraceae, and others), osteoporosis (genus *Pseudomonas*, genus *Methylobacterium*), decreased liver function (genus *Campylobacter* and others), yellowish skin (genus *Bacillus*, bacterium *Rothia dentocariosa*, and others), diabetes (a bacterium belonging to order Actinomycetales).

The aged skin index, which is computed from the presence or absence of sagging, wrinkles, non-resilience, and the like of the facial skin, was found to show a correlation with the abundance of a series of bacteria which may be referred to as "aged skin bacteria," including bacterial species belonging to class Gammaproteobacteria, bacterium *Propionibacterium granulosum*, and others.

BRIEF DESCRIPTION OF THE DRAWINGS

FIG. 16 shows results from multiple regression analysis of various bacterial species present in the bacterial floras from the 1074 subjects for analyzing whether the relative amounts thereof and actual age correlate with various physical symptoms, and also lists physical symptoms with which the amount of a bacterium shows statistically significant correlation.

PREFERRED MODE FOR CARRYING OUT THE INVENTION

Figure 1:
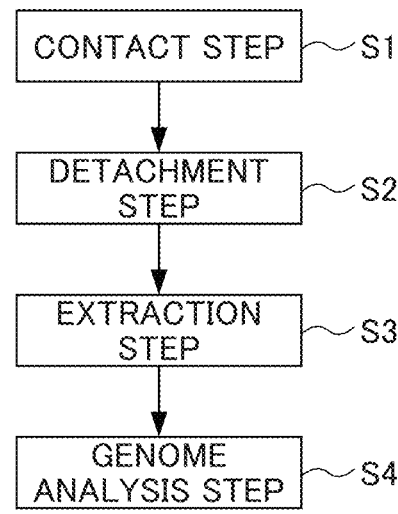
FIG. 1 shows an operation flow chart for the method of measuring a bacterial flora according to an embodiment of the present invention.

Below, the embodiments of the present invention will be described, but the present invention shall not be limited to these.

One embodiment of the present invention is a method of evaluating a physical condition of a subject, the method including the step of: determining a value of an abundance proportion of a skin indigenous microorganism on a skin surface of the subject among a skin microbial flora collected from the skin surface or a parameter based on the abundance proportion, a correlation criterion of the abundance proportion with the physical condition being pre-established, and then comparing the value with the correlation criterion. This enables various physical conditions to be accurately evaluated. Further, certain physical conditions which have been traditionally recognized in a collective manner may be subdivided by virtue of the abundance proportion or parameter of a skin indigenous microorganism, thereby improving a physical condition of a subject in a more reliable fashion.

Another embodiment of the present invention is a method of presenting information to a subject, the method including the steps of: evaluating a physical condition of the subject by the aforementioned method of evaluation, and presenting, when the physical condition is evaluated to be outside a target condition, information registered in a data base as an ingredient capable of directing the value of the abundance proportion or parameter toward a numerical range of an abundance proportion or parameter obtained based on the correlation criterion when the physical condition were within the target condition. This enables information for improving a physical condition and the like to be personalized and presented to a subject. It is noted that the term "information" as used herein encompasses the identity, directions, and dosage of an ingredient or a formulation containing the ingredient, the way and extent of expected improvement in a physical condition, and an adverse effect of the ingredient or formulation.

In an embodiment, the followings are preferably further included: a step of re-evaluating the physical condition of the subject after consumption of the ingredient by the aforementioned method of evaluation; and updating the information based on the extent of improvement in the physical condition after the re-evaluation. Thereby, the information in the data base can be improved, leading to more reliable improvement of a physical condition and others.

There is no particular limitation for the timing of re-evaluation, but, for example, the re-evaluation may be performed when a period of time likely enough to improve a physical condition in response to the use of an ingredient has passed, which may be included in the information in the data base.

Another embodiment of the present invention is a method of screening for a substance capable of improving or preventing a physical condition, the method including the step of: selecting a candidate substance based on how the candidate substance changes the value of an abundance proportion of a skin indigenous microorganism on a skin surface or a parameter based on the abundance proportion, a correlation criterion of the abundance proportion or parameter with the physical condition being pre-established. This can likely increase a probability of screening for a substance capable of improving or preventing a physical condition.

It is noted that the term "screening" as used in an embodiment of the present invention means that the probability of the presence of a substance capable of improving or preventing a physical condition is higher in the group of candidate substances after the screening method than in those before the screening method, but a candidate substance may not necessarily be actually capable of improving or preventing a physical condition. Therefore, it is preferred to further perform a step of examining whether a screened candidate substance can actually improve or prevent a physical condition.

The skin indigenous microorganism may be a bacterium or a fungus, but a bacterium is particularly preferred. The abundance proportion thereof may be in terms of any of phylum, class, order, family, genus, or species. For example, it may be an abundance proportion of at least one bacterium selected from the group consisting of bacteria belonging to phylum Actinobacteria, bacteria belonging to phylum Proteobacteria, and bacteria belonging to phylum Firmicutes. Among these, the abundance proportion of bacterium *P. acnes* may be mentioned.

There is no particular limitation for the parameter as long as it is based on the abundance proportion of a skin indigenous microorganism. The parameter may be the difference, sum, product, or ratio of the abundance proportions of a plurality of skin indigenous microorganism, or a combination thereof. In particular, the parameter may be the ratio, difference, or a combination thereof. For example, the difference in the relative amounts of a bacterial species belonging to phylum Proteobacteria and a bacterial species belonging to phylum Firmicutes may be mentioned. Alternatively, the parameter may be a diversity index of skin indigenous microorganisms.

There is no particular limitation for the physical condition as long as it shows correlation with the abundance proportion of a skin indigenous microorganism on a skin surface or a parameter based on the abundance proportion, but it can be a condition related to any part such as skin, hair, teeth, urine, bone, internal organs, blood, urine, and nerve. Skin conditions include skin age; oily skin; pimpled skin; spots, dullness, sagging, wrinkles, resilience conditions, pore conditions of the skin; yellowish skin; and the like. Hair conditions include thin hair, hair loss, and the like. Teeth conditions include periodontal disease, alveolar pyorrhea, and the like. Conditions of bone, internal organs, blood, urine, and nerve include liver functions, high uric acid, knee pain, osteoporosis, autonomic imbalance, diabetes, and the like. In addition, the physical condition encompasses menopause which may affect female hormone and aesthetic properties.

The term "correlation criterion" refers to a criterion which can qualitatively or quantitatively determine the goodness or seriousness of a physical condition to be evaluated based on the value of the aforementioned abundance proportion or parameter determined for a skin microbial flora.

Many of physical conditions may correlate with not only a skin microbial flora but also an extra phenomenon (for example, actual age). For this reason, an effect from at least one phenomenon known to correlate with a physical condition is preferably removed from the correlation criterion. This can reduce an effect from the presence or absence and the extent of the aforementioned extra phenomenon about a subject, enabling more accurate evaluation of a physical condition based on the value of the abundance proportion or parameter of a skin microbial flora. Further, according to the method of presenting information to a subject, more suitable information can be presented considering the presence or absence and the extent of the above extra phenomenon about a subject. For this reason, the presence or absence and the extent of the above extra phenomenon about the subject is preferably input in addition to the abundance proportion or parameter. Further, in the method of screening for a substance capable of improving or preventing a physical condition, a substance which may improve or prevent a physical condition tends to be obtained more easily regardless of the above extra phenomenon about a user.

Moreover, the correlation criterion may be created for a sub-population into which a population is categorized according to at least one selected from the group consisting of age, sex, residential area, nationality, and race. By this, a physical condition can be accurately evaluated even considering the age, sex, residential area, nationality, race, and the like of a subject. Further, according to the method of presenting information to a subject, more suitable information can be presented considering the age, sex, residential area, nationality, race of the subject. For this reason, at least one selected from the group consisting of the age, sex, residential area, nationality, race of a subject is preferably input in addition to the abundance proportion or parameter. Moreover, in the method of screening for a substance capable of improving or preventing a physical condition, a substance which may improve or prevent a physical condition and be suitable for the age, sex, residential area, nationality, race of a user tends to be obtained more easily.

There is no particular limitation for the location from which a skin microbial flora is collected, but it may be the face, scalp, armpit, navel, and the like. Among these, the face, in particular the forehead can be mentioned. It is noted that a location from which a sample is collected for a subject preferably coincides with a location from which samples were collected for a population where a correlation criterion was created.

EXAMPLES

Example 1

Questionnaire studies including items of age, skin type, and the like were conducted for 1,100 Japanese women aged 18 to 69 randomly selected from every prefecture except for Okinawa. Further, women who participated in the questionnaire studies were each analyzed for a bacterial flora on the facial skin in accordance with the following method at the same time as the questionnaire.

(Questionnaire)

The questionnaire was filled via Internet just before sampling was performed.

(Analysis of Bacterial Flora)

A bacterial flora was analyzed according to the flow chart shown in FIG. 1.

Contact Step S1 and Detachment Step S2

Figure 2:
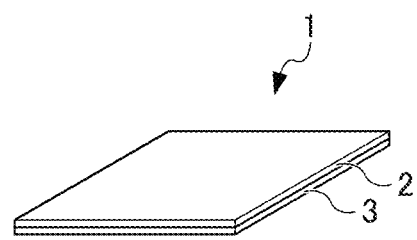
FIG. 2 shows a perspective view of an adhesive tape for use in an embodiment of the present invention.

An adhesive tape 1 shown in FIG. 2 is prepared. The adhesive tape 1 has a structure in which an application layer 3 including an adhesive is provided on a tape base material 2 as a thin film base. Therefore, it can adhere to the human skin as in a common adhesive bandage and a dressing tape, facilitating the contact step S1. The adhesive tape 1 attached to a release paper (not shown) and enclosed in a re-sealable aluminum bag along with a desiccating agent was send to a subject along with latex gloves. A subject was instructed to wear the latex gloves immediately after getting up, and then open the aluminum bag to take out the release paper to which the adhesive tape 1 was attached, and then remove the adhesive tape 1, and apply it on the forehead. Subsequently, the adhesive tape 1 was allowed to adhere for 5 minutes, and then removed from the forehead, and placed back on the release paper. This was placed in the aluminum bag along with the desiccating agent, and the bag was then re-sealed. Subsequently, it was stored frozen until DNA analysis tests were performed.

Extraction Step S3

DNA was extracted directly from the adhesive tape 1 in accordance with the method by Morita et al. (*Microbes Environ*. Vol. 22, No. 3, 214-222, 2007) to prepare a DNA solution.

Genome Analysis Step S4

The 16S ribosomal RNA gene contained in the solution was amplified by the PCR method using the DNA solution obtained as described above, and then DNA analysis was performed with a sequencer (NGS) (Product name: MiSeq, Illumina inc.).

Results obtained in this way were analyzed using a pipeline analyzing tool Qiime. Then, bacteria are categorized according to phylum, and a relation between the abundance proportion and age was investigated for bacteria of phylum Actinobacteria, phylum Proteobacteria, phylum Firmicutes, and phylum Bacteroidetes.

Results

Figure 3:
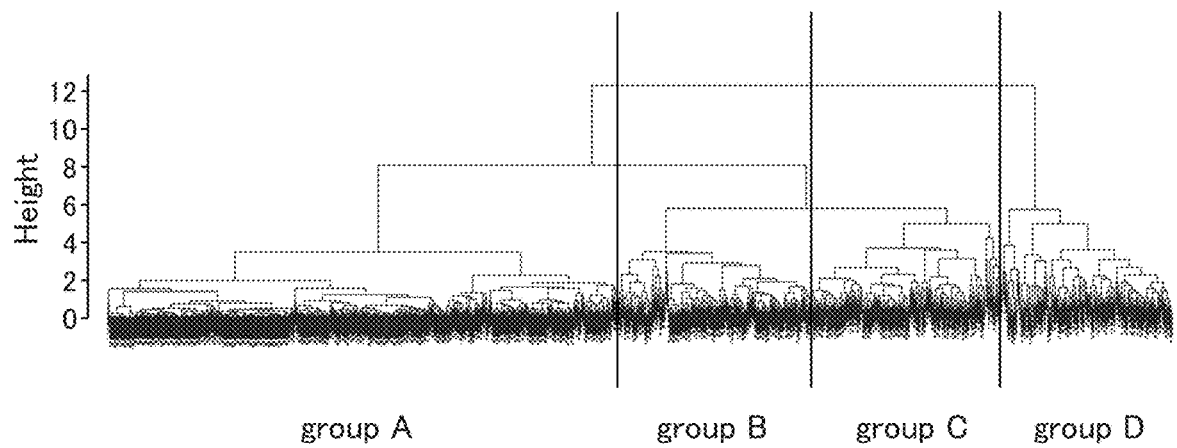
FIG. 3 shows results from clustering analysis of the skin bacterial floras collected from the foreheads of 1074 Japanese women based on the degree of dissimilarity between specimens (the weighted UniFrac distance).

First, reciprocal relations among facial bacterial floras obtained from the 1074 subjects were evaluated using the degree of dissimilarity between specimens (Weighted UniFrac distance) as an index. FIG. 3 shows results from clustering analysis based on the Weighted UniFrac distance. Results showed that the specimens were categorized roughly into four groups. Among these, approximately the half of the specimens were found to be categorized into the largest group, and the differences within the group were found to be relatively small.

Figure 4:
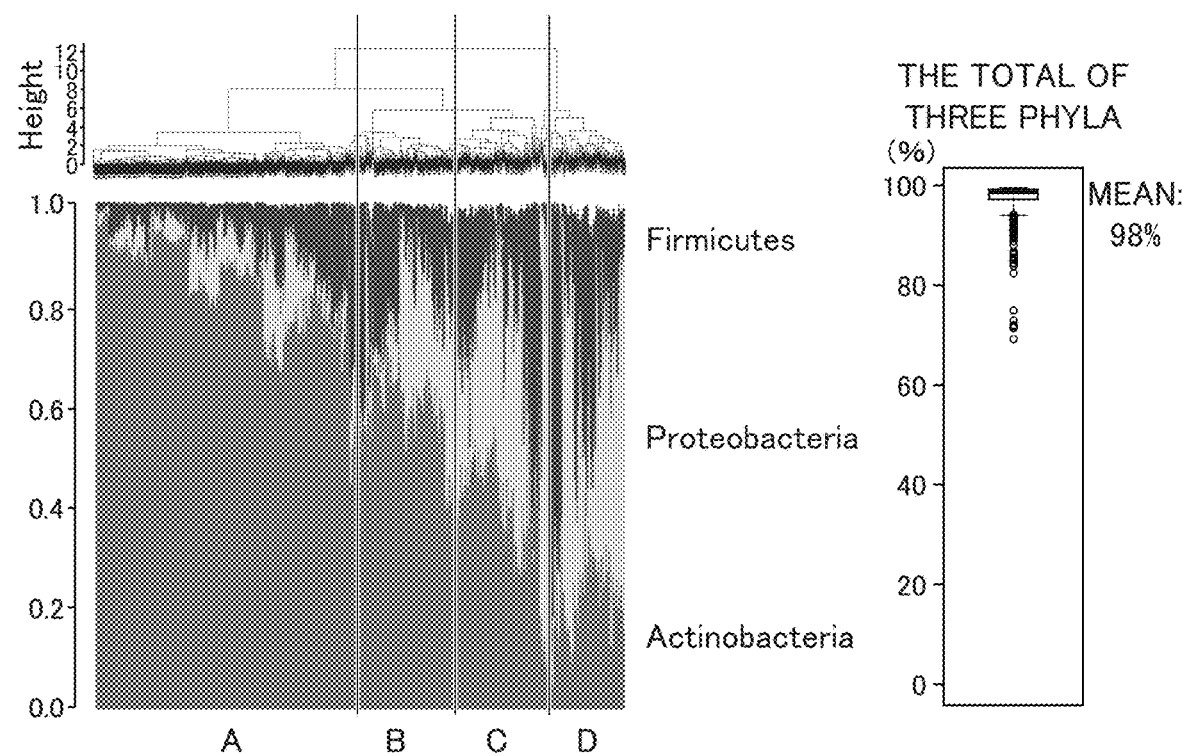
FIG. 4 shows a graph for visualizing the contents of bacterial species contained in the bacterial floras from the 1074 subjects at the phylum level.

The breakdown of constituent species in the bacterial floras was investigated. FIG. 4 visualizes the constituent breakdown at the phylum level. Bacteria belonging to three phyla, Actinobacteria, Protepbacteria, and Firmicutes accounted for most of the facial bacterial floras. The amount of phylum Actinobacteria as the most abundant constituent species was found to vary mostly according to the grouping observed in the clustering analysis.

Figure 5:
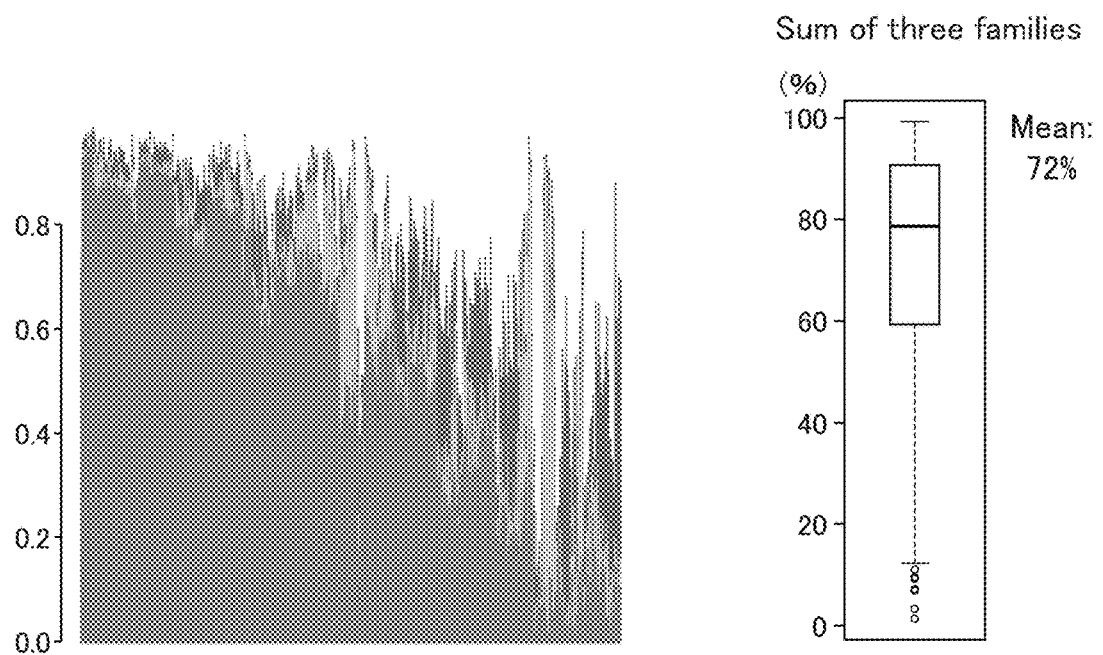
FIG. 5 shows a graph for visualizing the contents of bacterial species contained in the bacterial floras from the 1074 subjects at the family level (the top three bacterial species are shown).

FIG. 5 shows results from similar analysis performed at the family level as a lower taxon. Three abundant families were family Propionibacteriaceae of phylum Actinobacteria, family Xanthomonadeceae of phylum Proteobacteria, and family Staphylococcaceae of phylum Firmicutes. These families accounted for 72% of the bacterial floras on average. It is noted that a well-known skin indigenous bacterium *Staphylococcus epidermidis* is included in family Staphylococcaceae.

Figure 6:
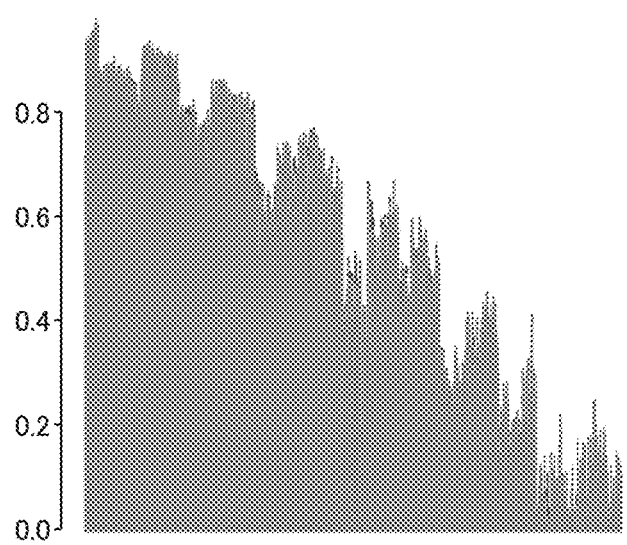
FIG. 6 shows a graph for displaying the contents of bacteria from phylum Actinobacteria contained in the bacterial floras from the 1074 subjects at the species level.

The most abundant constituent family Propionibacteriaceae was further investigated. Results showed that a bacterial species *Propionibacteria acnes* (hereinafter may be referred to as *P. acnes*, a so-called acne bacterium) accounted for most of the family (FIG. 6).

Figure 7:
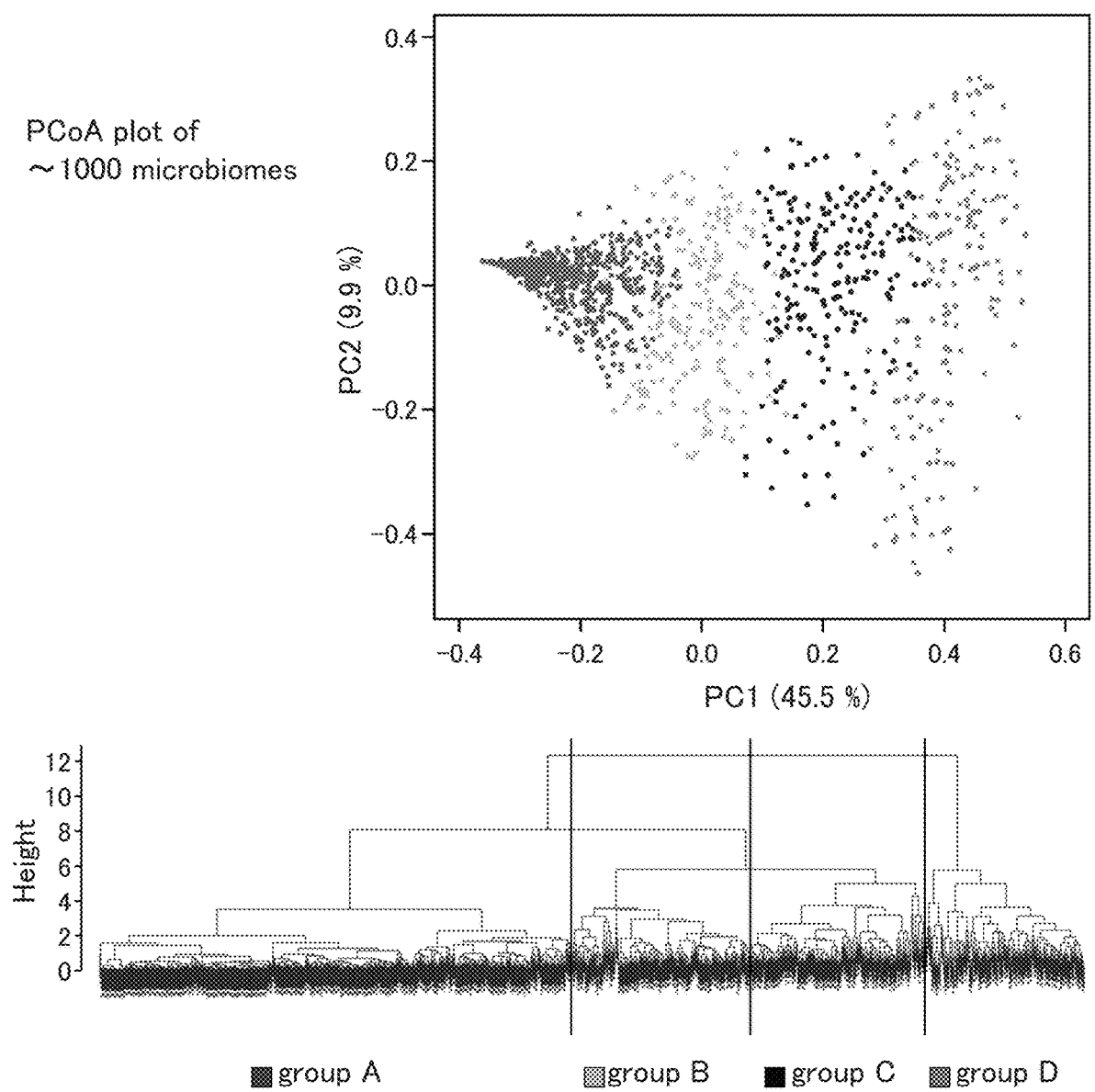
FIG. 7 shows results from the principal coordinate analysis of the bacterial floras from the 1074 subjects based on the weighted UniFrac distance.

In order to investigate which parameter can be used to represent a property of an individual's bacterial flora, the information about the Weighted UniFrac distances between specimens was analyzed in accordance with the approach of principal coordinate analysis. The results (FIG. 7) showed that specimens can be well represented as a distribution on a two-dimensional plane. The groups obtained from the clustering analysis are also clustered in this distribution map, demonstrating the validity of this distribution.

Figure 8:
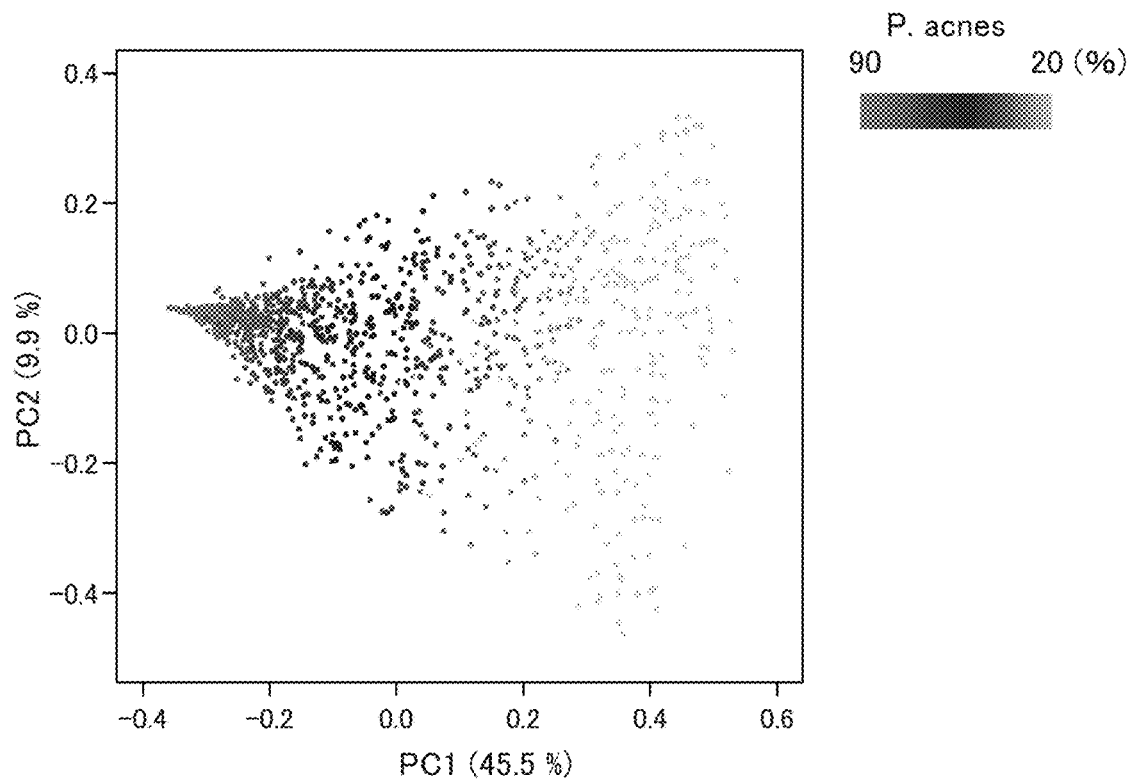
FIG. 8 shows that one of the coordinate axes found in the principal coordinate analysis corresponds to the relative amount of bacterium *Propionibacterium acnes*.
Figure 9:
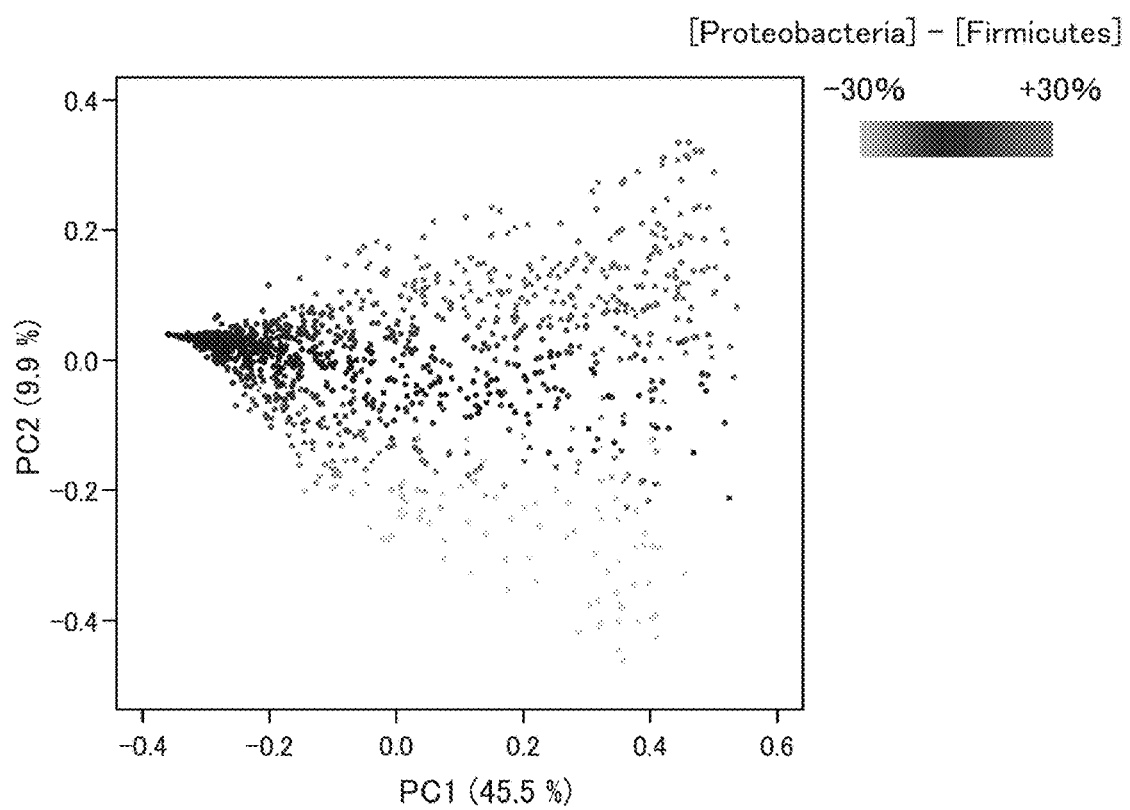
FIG. 9 shows that another coordinate axis found in the principal coordinate analysis corresponds to the difference in the relative amounts of phylum Proteobacteria and phylum Firmicutes.

Each coordinate axis of the two-dimensional distribution map obtained from the principal coordinate analysis was studied to elucidate which property of a bacterial flora was represented by it. Results showed that the first axis well correlated with the total abundance of bacterium *P. acnes* in the bacterial floras (FIG. 8). Further, the second axis showed a good correlation with an index (hereinafter, may be referred to as the P-F amount) which represented the difference in the relative amounts of a bacterial species belonging to phylum Proteobacteria and a bacterial species belonging to phylum Firmicutes (FIG. 9). These results showed that the amount of bacterium *P. acnes* and the P-F amount can be mentioned as an index for representing a property of each bacterial flora.

Example 3

Figure 10:
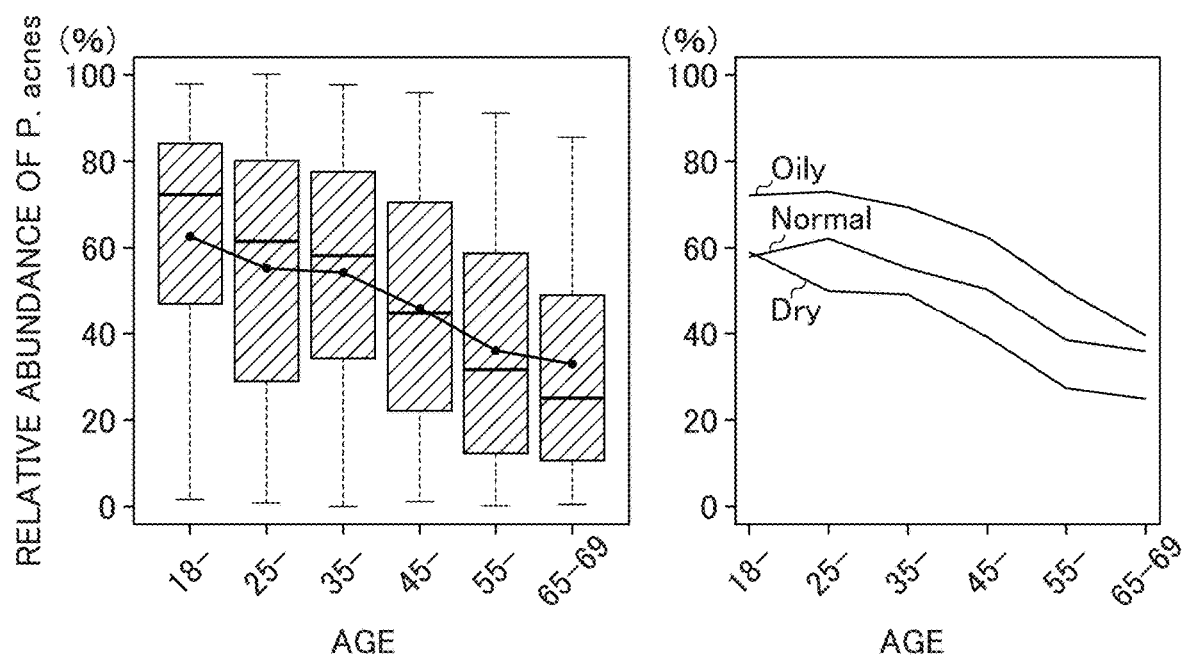
FIG. 10 represents graphs showing that the relative amount of bacterium *Propionibacterium acnes* correlates with actual age and skin oiliness.

Host factors which determine the amount of bacterium *P. acnes* as the most abundant bacterial species were searched. Results showed that the relative amount of bacterium *P. acnes* correlated with the actual age, and the amount of bacterium *P. acnes* decreased as the age increased (the left panel in FIG. 10. Box-and-whisker plots. Red represents the average values of the age groups.). Further, the amount of bacterium *P. acnes* also showed a correlation with skin oiliness. According to both age and skin types (oily, normal, dry), 1074 individuals were grouped, and the mean value of the amount of bacterium *P. acnes* was calculated for each group, and then plotted (the right panel in FIG. 10). Results reveled that the amount of bacterium *P. acnes* also correlated with skin oiliness independently from age.

(Relation Between Amount of Bacterium *P. acnes* and Pimples)

Figure 11:
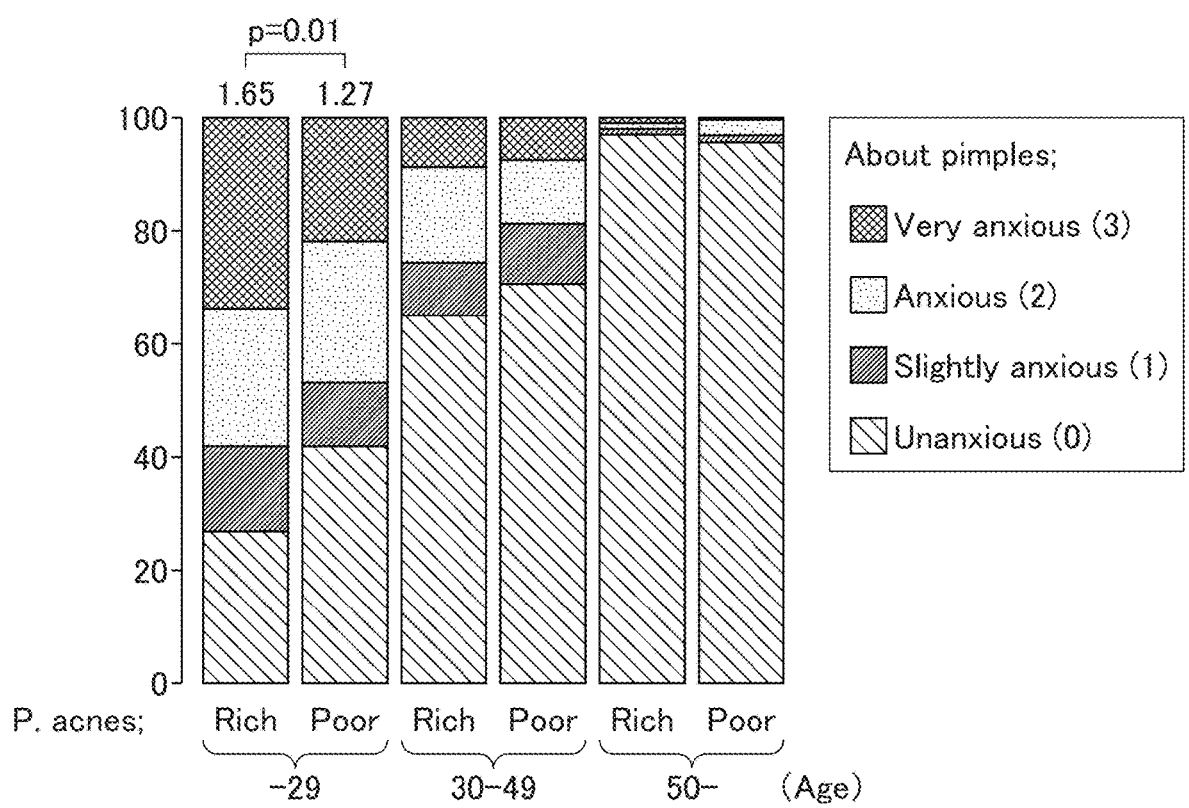
FIG. 11 represents a graph showing that the amount of bacterium *Propionibacterium acnes* correlates with the seriousness of symptoms of pimples in the youth segment.

The relative amount of bacterium *P. acnes* was found to correlate with the development and intensity of symptoms of pimples. The amount of *P. acnes* was found to correlate with age as described as above, and pimples represent a disease which often affects the youth segment. Therefore, the specimens were analyzed after categorized into three groups: youth (29 years old or less), middle age (30 years old or more and 49 years old or less), and elderly (50 years old or more) to eliminate age-related effects. Symptoms of pimples were scored based on results from the self-evaluation questionnaire (very bothered by pimples (3 points); bothered (2 points); somewhat bothered (1 point); and not bothered (0 point)). Results showed a significant difference in the intensities of symptoms in the youth segment between a group having more bacterium *P. acnes* (the relative amount was 70% or more) and a group having less bacterium *P. acnes* (FIG. 11). The amount of *P. acnes* was found to correlate with the development and aggravation of symptoms of pimples.

(Relation Between Amount of Bacterium *P. acnes* and Expanded Pores)

Figure 12:
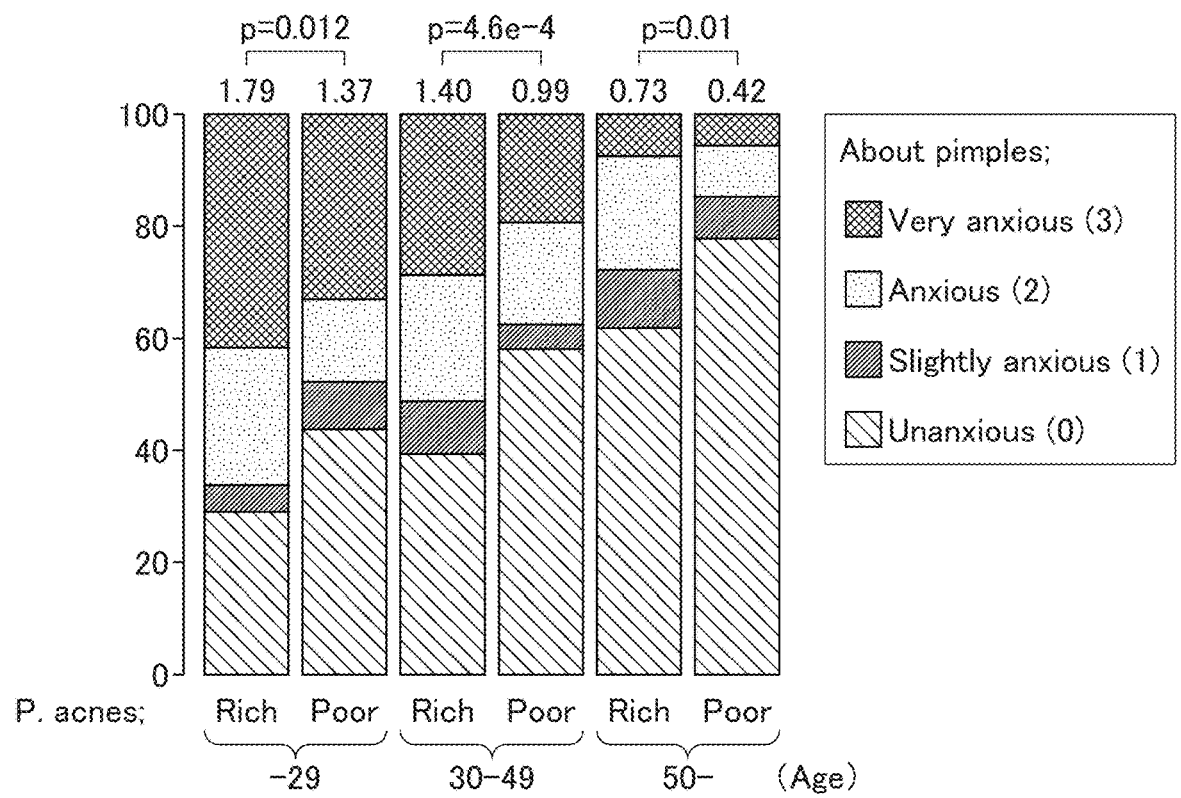
FIG. 12 represents a graph showing that the amount of bacterium *Propionibacterium acnes* correlates with expanded pores.

Similar analysis showed that there also existed a correlation between the amount of *P. acnes* and expanded pores (FIG. 12). Expanded pores were scored based on results from the self-evaluation questionnaire (very bothered (3 points); bothered (2 points); somewhat bothered (1 point); and not bothered (0 point)). In all the segments of youth, middle age, and elderly, the scores of expanded pores were found to be bad when the amount of *P. acnes* was large.

Example 4

(Relation Between P-F Amount and Pimples)

Figure 13:
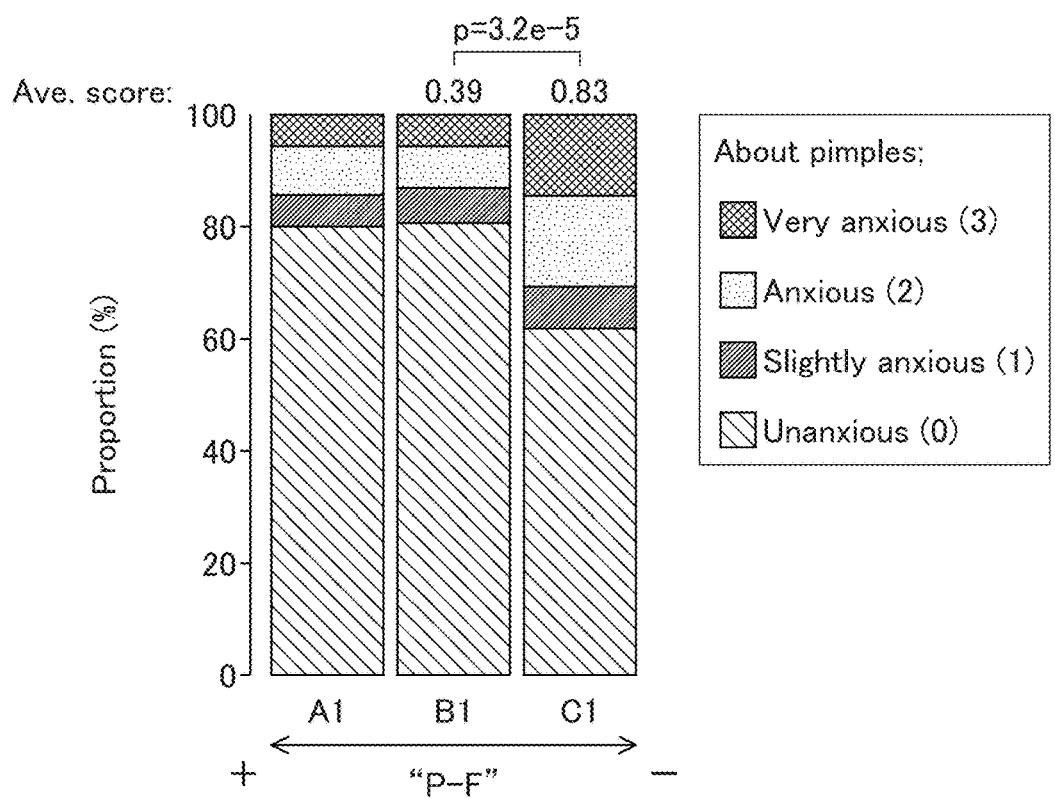
FIG. 13 represents a graph showing that the difference in the relative amounts of a bacterial species belonging to phylum Proteobacteria and a bacterial species belonging to phylum Firmicutes correlates with the seriousness of symptoms of pimples.

Next, the P-F amount (the difference in the relative amounts of a bacterial species belonging to phylum Proteobacteria and a bacterial species belonging to phylum Firmicutes) was also found to correlate with the symptoms of pimples. Specimens categorized into three groups according to the P-F amount revealed that a group having a smaller value (specimens having more phylum Firmucutes than phylum Proteobacteria) correlated with more intense symptoms of pimples (FIG. 13). It is noted that the P-F amount did not correlate with age, and thus the age-effect removing treatment was omitted.

(Relation Between P-F Amount and Thin Hair/Hair Loss)

Figure 14:
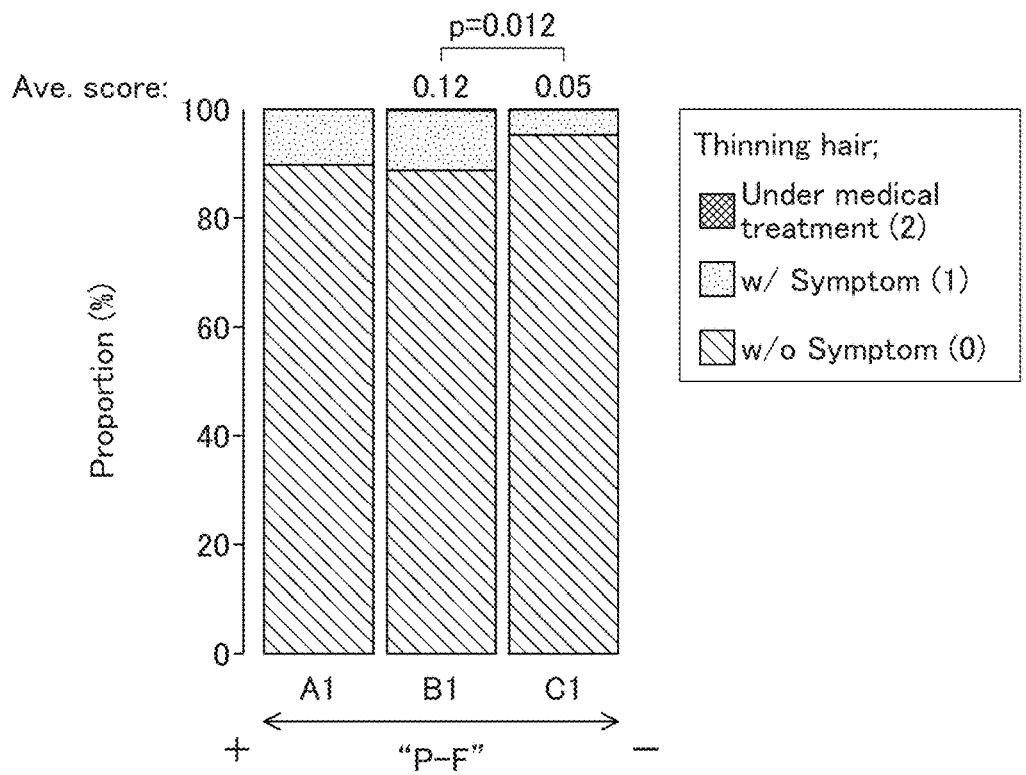
FIG. 14 represents a graph showing that the difference in the relative amounts of a bacterial species belonging to phylum Proteobacteria and a bacterial species belonging to phylum Firmicutes correlates with the occurrence of thin hair/hair loss in the head.

The P-F amount was also found to correlate with symptoms of thin hair/hair loss. Symptoms of thin hair/hair loss were scored based on results from the self-evaluation questionnaire as follows: under treatment of thin hair/hair loss (2 points); having a symptom of thin hair/hair loss (1 point); having no symptom of thin hair/hair loss (0 point). In a group having a smaller P-F amount, significantly less people complained symptoms of hair-loss (FIG. 14). This demonstrates that the spectrum of a facial skin bacterial flora can be related to a physical symptom other than that of the face.

(Relation Between P-F Amount and Periodontal Disease/Alveolar Pyorrhea)

Figure 15:
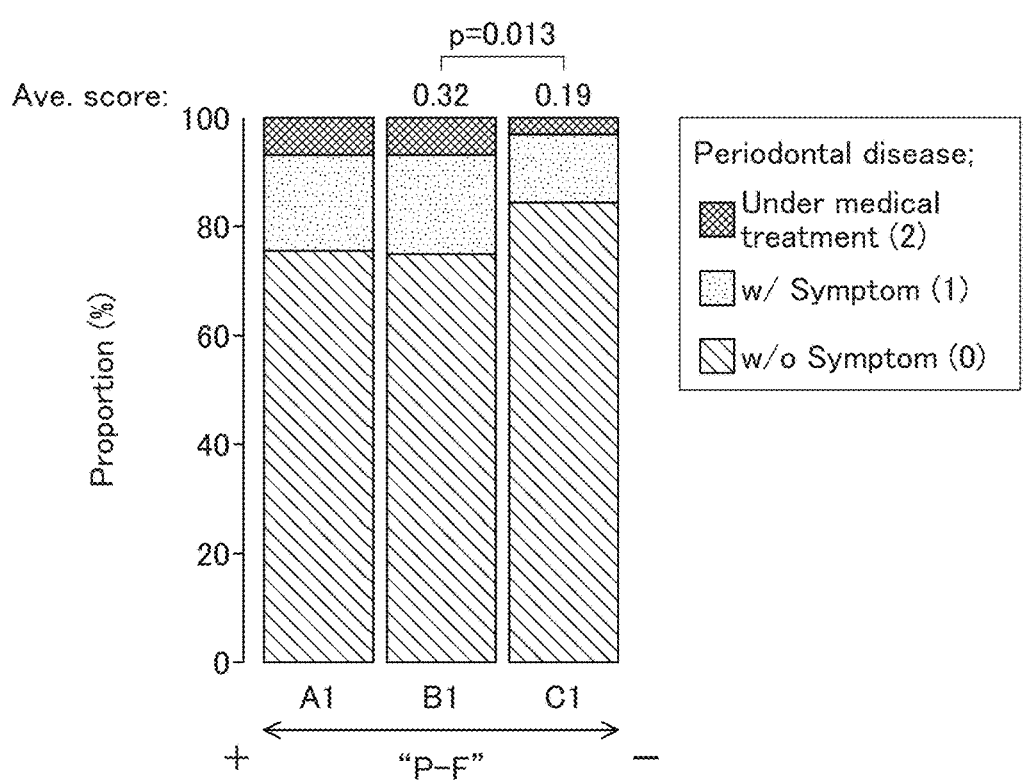
FIG. 15 represents a graph showing that the difference in the relative amounts of a bacterial species belonging to phylum Proteobacteria and a bacterial species belonging to phylum Firmicutes correlates with the development of alveolar pyorrhea/periodontal disease.

The P-F amount was also found to correlate symptoms of periodontal disease/alveolar pyorrhea. Symptoms of periodontal disease/alveolar pyorrhea were scored based on results from the questionnaire as follows: under treatment of periodontal disease/alveolar pyorrhea (2 points); having a symptom of periodontal disease/alveolar pyorrhea (1 point); having no symptom of periodontal disease/alveolar pyorrhea (0 point). As shown in FIG. 15, a group having a smaller P-F amount showed significantly fewer symptoms of periodontal disease/alveolar pyorrhea.

A possible correlation between information about species as a taxon lower than phylum and physical symptoms were also analyzed. The relative amount of each bacterial species identified in the bacterial floras and the numericalized/scored results from the questionnaire were evaluated for a correlation. At that time, a correlation between the amount of a bacterium and a physical symptom from which age-related effects were removed was detected by investigating a relation of the two variables, the amount of the bacterium and the actual age, with the physical symptom using multiple regression analysis. This is because some physical symptoms were known to correlate with actual age. Considering it was a multiple test, the Benjamini-Hochberg method was used to adjust the false-positive detection rate to be 10%. As a result, only correlations having a statistically significant difference as high as $p=6\times10^{-4}$ or less were extracted. The results obtained are summarized in FIG. 16. Here, bacterial species which showed correlations are summarized for each of various diseases/symptoms of the body and skin. The following correlations were found: for example, freckles and the amount of bacterium *Corynebacterium kroppenstedti*; the amounts of genus *Bacillus* and bacterium *Rothia dentocariosa* and yellowish skin; the amounts of bacteria belonging to genus *Rothia*, genus *Brevibacterium*, and others and high uric acid values; the amounts of bacteria belonging to genus *Pseudomonas* and genus *Methylobacterium* and osteoporosis; and the amounts of bacteria belonging to genus *Microbacterium* and thin hair/hair loss; and others. This showed that relations with various physical diseases/symptoms can be found by extracting useful information from the data of bacterial floras.

(Diversity of Bacterial Flora, and Correlations with Physical Symptoms)

Figure 17:
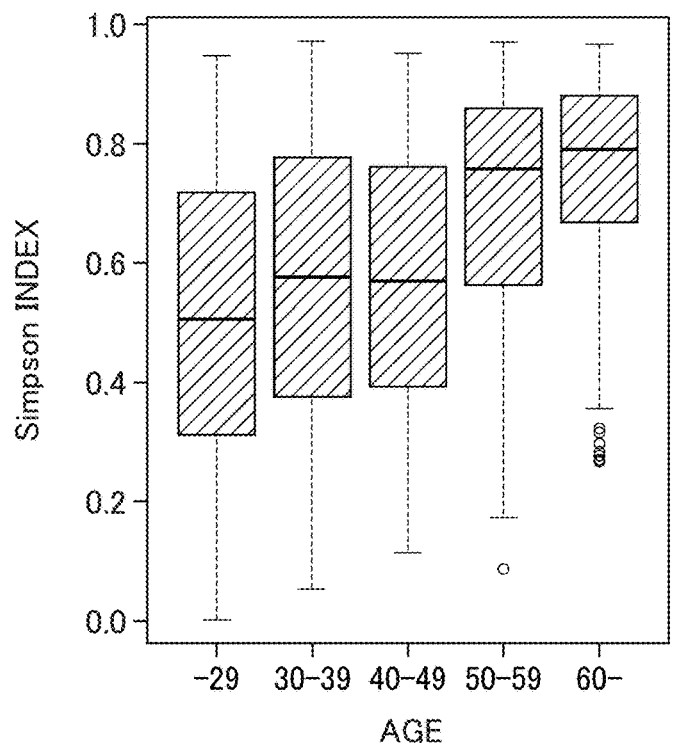
FIG. 17 represents a graph showing that the diversity index (the Simpson index) of a bacterial flora correlates with actual age.
Figure 18:
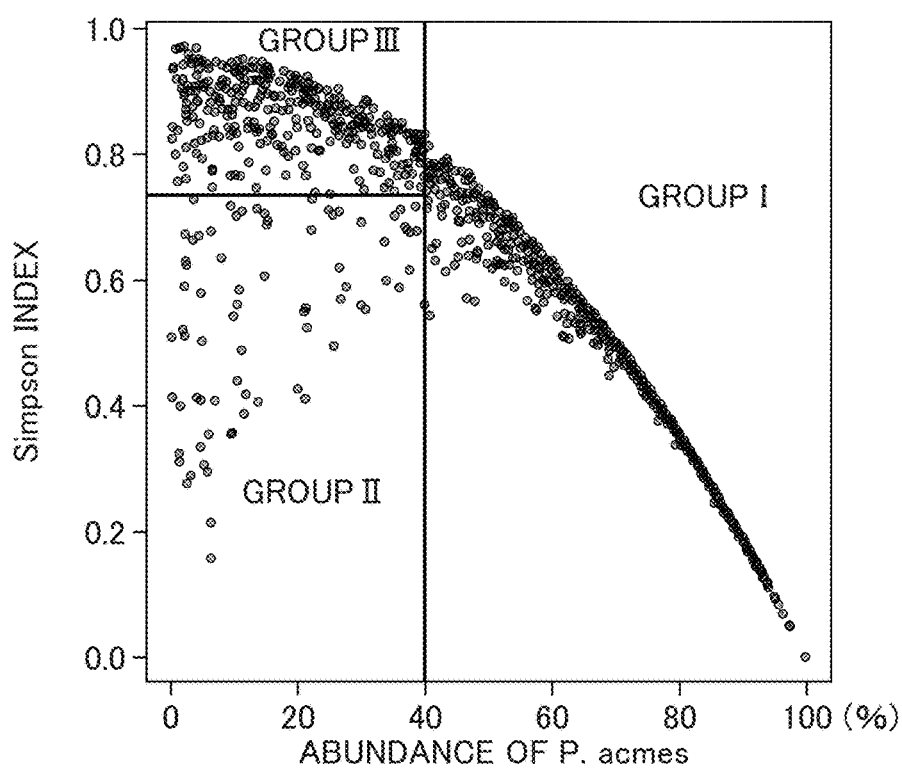
FIG. 18 represents a graph showing that bacterial floras can be categorized according to the amount of bacterium *Propionibacterium acnes* and the diversity of a bacterial flora.
Figure 19:
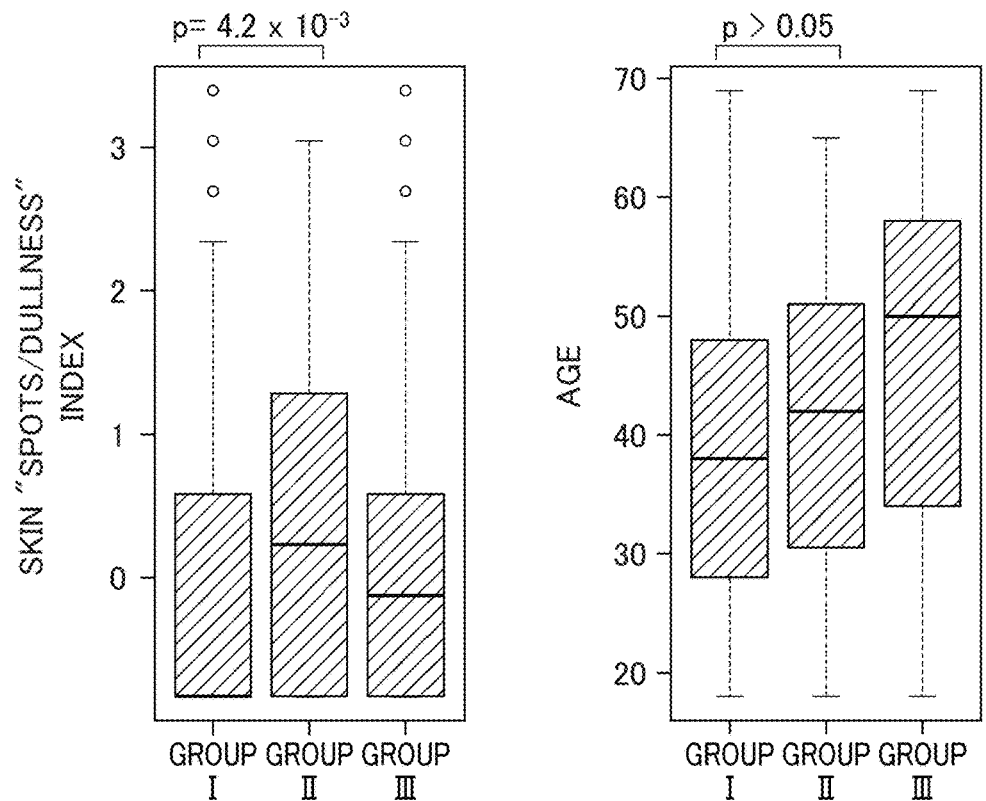
FIG. 19 shows that a bacterial flora having poor diversity in spite of a smaller amount of bacterium *Propionibacterium acnes* is related with the skin with problems such as spots and/or dullness.

In addition to the amount of a bacterium, the diversity of a bacterial flora was also found to serve as an index showing a correlation with a physical symptom. The diversity of a bacterial flora within each specimen is known to be able to be expressed in terms of the Simpson index. First, the Simpson index and actual age were investigated for a correlation. Results showed that the Simpson index increased, that is, the diversity of a bacterial flora increased, as the age increased (FIG. 17). Then, use of the two parameters, the above diversity index and bacterium *P. acnes*, showed that the structure of a bacterial flora of each specimen may be categorized into three groups (FIG. 18). That is, they are a group (group I) having more bacterium *P. acnes* (and low diversity), a group (group II) having a less amount of bacterium *P. acnes* but showing lower diversity, and lastly a group (group III) having a less amount of bacterium *P. acnes* and showing higher diversity. A possible correlation with results from the questionnaire was studied by examining the presence or absence of a physical symptom specific to each of the groups. Results showed there was a good correlation with the total score of three questionnaire results: spots, freckles, and dullness of the skin (FIG. 19). Many individuals in the group II complained symptoms of "spot/dullness" (having a high "spot/dullness" index), and the difference from the group I was statistically significant. This difference was not due to the difference in the age distributions of those who constitute the groups (the difference in age was not statistically significant).

(Relation Between Skin Aging and Skin Bacterial Flora)

Figure 20:
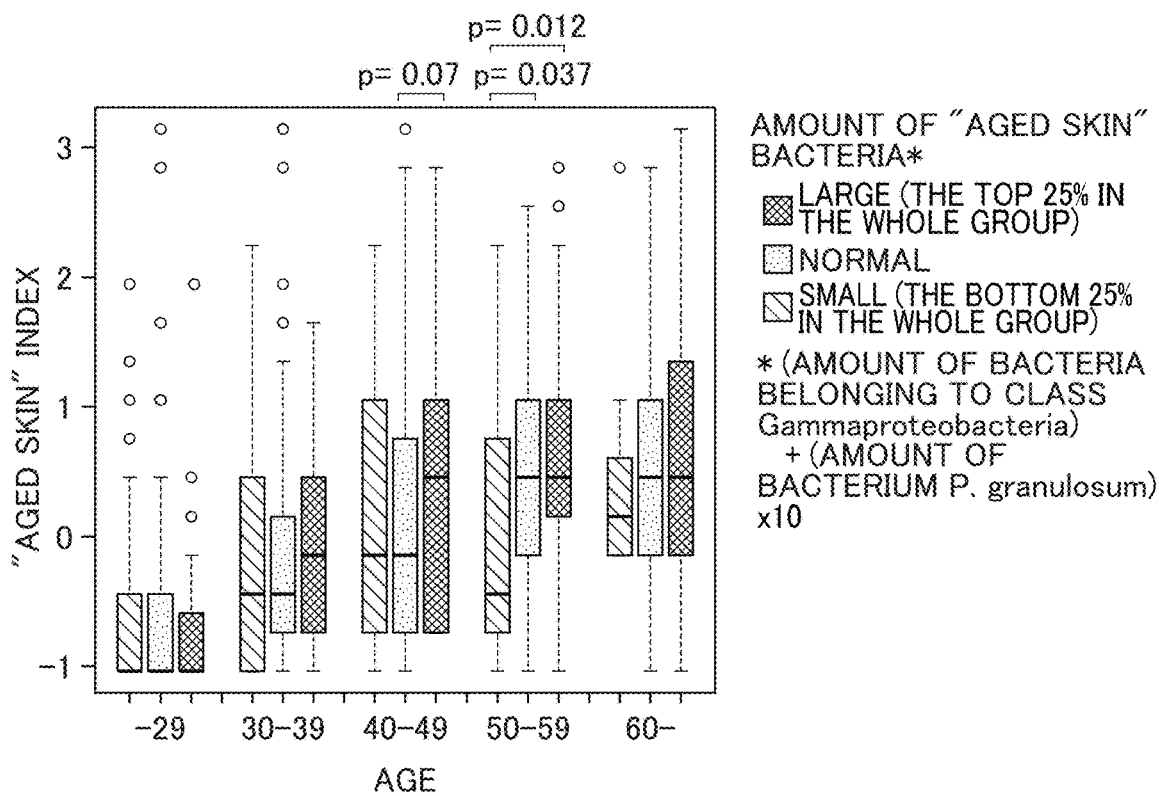
FIG. 20 shows that the amount of aged skin bacteria correlates with the aged skin index (an index for representing overall wrinkles, sagging, and non-resilience, and the like) in the 50's segment.

Items likely related to skin aging (for example, lack of skin elasticity, sagging cheek, and the like) were also included in the items of the questionnaire. Accordingly, a bacterial species showing a correlation with in particular any of these items was tried to be detected. For each of the results from 14 items in the questionnaire: "Sagging/loose eyelid and tail of eyes," "spots (due to aging and imbalanced hormone)," "lack of skin resilience," "lack of skin elasticity," "sagging cheek," "hollow/thin cheek," "fine wrinkles near the month," "nasolabial fold (sulcus nasolabialis)," "sagging/downturned angle of mouth," "forehead wrinkles," "wrinkles between eyebrows," "neck wrinkles," "yellowish skin," "sagging/loose face line (outline)," the "aged skin" index was computed according to a method in which one point was added when the answer was "bothered by a symptom." The above index was found to show a good correlation with the abundance of two bacterial species (a bacterial species from class Gammaproteobacteria and bacterium *Propionibacterium granulosum*). The results are shown in FIG. 20. The vertical axis represents the normalized aged skin index. Specimens are grouped according to age and the abundance of above bacterial species. For categorization according to the amount of bacteria, used was the sum (referred to as the amount of "aged skin" bacteria) of the relative abundance of class Gammaproteobacteria and 10 times of the relative abundance of bacterium *Propionibacterium granulosum*. They were categorized into three groups: those who have a value of the sum in the top 25%; who have a value of the sum in the bottom 25%; and those who have a value other than these. Results showed that a group with a smaller amount of aged skin bacteria had a significantly smaller aged skin index as compared with the other groups for individuals at their 50's. Similarly, for individuals at their 40's, there found a trend where a larger aged skin index corresponded to a larger amount of aged skin bacteria (p=0.07). These suggested that the abundance of aged skin bacteria correlated with differently progressed skin aging.

These results indicate that extracting useful information from the information included in the data of a bacterial flora enables evaluation of phenomena difficult for objective evaluation such as skin aging, and also enables contemplation of a preventive measure.

(Relation Between Amount of Bacterium *P. acnes* and Menopause)

Figure 21:
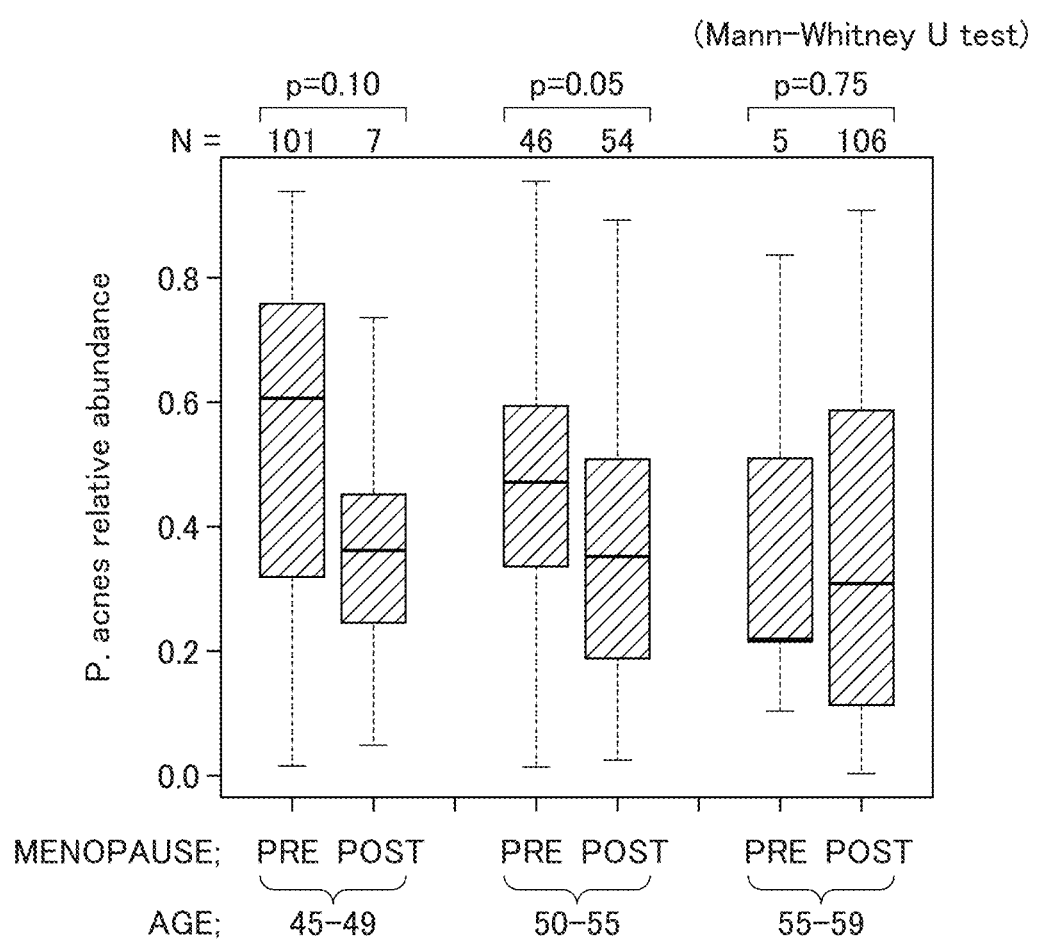
FIG. 21 represents a graph showing that the amount of bacterium *Propionibacterium acnes* correlates with menopause.

The amount of bacterium *P. acnes* was found to correlate with the presence or absence of menses. As described in the previous section, the amount of *P. acnes* correlates with age, and menopause is also a phenomenon related to age. In order to discriminate effects from age and menopause, individuals aged 45 or more and less than 60 were categorized into three groups according to age, and each group was further categorized into two groups of pre- and post-menopause. FIG. 21 represents box-and-whisker plots illustrating the distributions of the amounts of *P. acnes* found in each group. According to the results, a less amount of *P. acnes* was observed for a group of post-menopause and 50 years old or more and 54 years old or less, and the difference thereof was statistically significant. A similar trend was also observed for a group of 45 years old or more and 49 years old or less, but the statistical significance was not detected due to a fewer number of specimens of post-menopause corresponding to the above age range. In order to conduct more rigorous analysis, multiple regression analysis of individuals aged 40 or more and less than 60 using two descriptive variables of age and the presence or absence of menses and an target variable of the amount of P. acnes. According to the results, the amount of P. acnes was found to correlate with both age and menopause (the amount of P. acnes decreased as the age increased, and the amount of P. acnes was larger in a case of menopause). These correlations were found to be at a statistically significant level ($p=0.027$ for age, $p=0.037$ for menopause). These showed that the amount of P. acnes correlated with menopause.

The present invention shall not be limited to the above descriptions about the embodiments and Examples of the present invention in any sense. Various variations which a person skilled in the art would envisage without departing from the scope of the claims will be included in the present invention.

EXPLANATION OF REFERENCE NUMERALS

1 Adhesive tape
2 Tape base material
3 Application layer

The invention claimed is:

1. A method of improving or preventing a physical condition of a subject, the method comprising the steps of:
   determining a value of an abundance proportion of a skin indigenous microorganism on a skin surface of the subject among a skin microbial flora collected from the skin surface or a parameter based on the abundance proportion, a correlation criterion of the abundance proportion or parameter with the physical condition being pre-established, and then comparing the value with the correlation criterion,
   wherein the physical condition is
   a skin condition of at least one of skin age, freckles of skin, texture, yellowish skin, shininess, spots, dullness, sagging, wrinkles, and an aged skin index or
   a condition relating to at least one of hair, a tooth, a bone, an internal organ, blood, urine, and a nerve, excluding diabetes, presenting, when the physical condition is evaluated to be outside a target condition, information registered in a data base as an ingredient capable of directing the value of the abundance proportion or the parameter toward a numerical range of the abundance proportion or parameter obtained based on the correlation criterion when the physical condition is within the target condition; and
   administering the ingredient to the subject.

2. The method according to claim 1, further comprising the steps of: re-evaluating the physical condition of the subject by the method according to claim 1 after consumption of the ingredient, and
   updating the information based on the extent of improvement in the physical condition after the re-evaluation.

3. The method according to claim 2, wherein the physical condition is at least one selected from the group consisting of skin age, spots, dullness, sagging, wrinkles, thin hair, hair loss, periodontal disease, alveolar pyorrhea, menopause, liver function, high uric acid, knee pain, osteoporosis, autonomic imbalance, yellowish skin, and diabetes.

4. The method according to claim 2, wherein the correlation criterion is a correlation criterion between the physical condition and the abundance proportion or parameter after an effect from at least one phenomenon known to correlate with the physical condition is removed, wherein the correlation criterion is created for a sub-population into which a population is categorized according to age.

5. The method according to claim 1, wherein the abundance proportion is an abundance proportion of at least one bacterium selected from the group consisting of bacteria belonging to phylum Actinobacteria, bacteria belonging to phylum Proteobacteria, and bacteria belonging to phylum Firmicutes.

6. The method according to claim 1, wherein the parameter is at least one selected from the group consisting of a ratio or difference of the abundance proportions and a diversity index of skin indigenous microorganisms.

7. The method according to claim 1, wherein the physical condition is freckles of skin.

8. The method according to claim 1, wherein the physical condition is dullness.

9. The method according to claim 1, wherein the physical condition is sagging.

10. The method according to claim 1, wherein the physical condition is wrinkles.

11. The method according to claim 1, wherein the physical condition is aged skin index.

12. A method of improving or preventing a physical condition, the method comprising the steps of:
    selecting a candidate substance based on how the candidate substance changes a value of an abundance proportion of a skin indigenous microorganism on a skin surface or a parameter based on the abundance proportion, a correlation criterion of the abundance proportion or parameter with the physical condition being pre-established,
    wherein the physical condition is
    a skin condition of at least one of skin age, freckles of skin, texture, yellowish skin, shininess, spots, dullness, sagging, wrinkles, and an aged skin index or
    a condition relating to at least one of hair, a tooth, a bone, an internal organ, blood, urine, and a nerve, excluding diabetes; and
    administering the selected substance to the subject.

13. The method according to claim 12, wherein the abundance proportion is an abundance proportion of at least one bacterium selected from the group consisting of bacteria belonging to phylum Actinobacteria, bacteria belonging to phylum Proteobacteria, and bacteria belonging to phylum Firmicutes.

14. The method according to claim 12, wherein the parameter is at least one selected from the group consisting of a ratio or difference of the abundance proportions and a diversity index of skin indigenous microorganisms.

15. The method according to claim 12, wherein the physical condition is at least one selected from the group consisting of skin age; spots, dullness, sagging, and wrinkles.

16. The method according to claim 12, wherein the physical condition is at least one of thin hair, hair loss, periodontal disease, alveolar pyorrhea, and menopause.

17. The method according to claim 12, wherein the physical condition is at least one of liver function, high uric acid, knee pain, osteoporosis, autonomic imbalance, yellowish skin, and diabetes.

18. The method according to claim 12, wherein the correlation criterion is a correlation criterion between the physical condition and the abundance proportion or parameter after an effect from at least one phenomenon known to correlate with the physical condition is removed, wherein the correlation criterion is created for a sub-population into which a population is categorized according to age.

19. The method of claim 12, wherein the correlation criterion is a correlation criterion between the physical condition and the abundance proportion or the parameter after an effect from actual age is removed.

20. The method of claim 12, wherein the correlation criterion is a correlation criterion created for a sub-population into which a population is categorized according to an age of the population.

21. The method of claim 12, wherein the parameter is a difference, a sum, a product, or a ratio of the abundance proportions of a plurality of skin indigenous microorganisms, or a combination thereof.

22. The method of claim 12, wherein an abundance proportion of bacterium *Propionibacterium acnes* as the abundance proportion and a diversity index of skin indigenous microorganisms as the parameter are used in combination.

23. The method of claim 12, wherein the abundance proportion or the parameter correlates with a coordinate axis obtained by analysis of a degree of dissimilarity between bacterial floras from specimens.

24. The method of claim 12, wherein the physical condition is oily skin and the abundance proportion is an abundance proportion of bacteria belonging to family Xanthomonadaceae, genus *Sphingomonas*, genus *Vibrio*, family Aeromonadaceae, genus *Pseudoalteromonas*, class Gammaproteobacteria, genus *Streptococcus*, family Gemellaceae, genus *Acidocella*, family Planococcaceae, genus *Lautropia*, genus *Shewanella*, or genus *Granulicatella*; or bacterium *Pseudoalteromonas porphyrae* or bacterium *Roseomonas mucosa*.

25. The method of claim 12, wherein the physical condition is a condition of freckles and the abundance proportion is an abundance proportion of bacterium *Corynebacterium kroppenstedti*.

26. The method of claim 12, wherein the physical condition is a condition of texture of skin and the abundance proportion is an abundance proportion of bacterium *Propionibacterium acnes* or bacterium *Propionibacterium granulosum*.

27. The method of claim 12, wherein the physical condition is yellowish skin and the abundance proportion is an abundance proportion of bacteria belonging to genus *Bacillus*, genus *Actinomyces* or genus *Rothia* or bacterium *Rothia dentocariosa*.

28. The method of claim 12, wherein the physical condition is a liver function and the abundance proportion is an abundance proportion of bacteria belonging to genus *Campylobacter* or genus *Bacillus*, or bacterium *Streptococcus anginosus*.

29. The method of claim 12, wherein the physical condition is a high uric acid value and the abundance proportion is an abundance proportion of bacteria belonging to genus *Rothia*, genus *Brevibacterium*, family Erythrobacteraceae or family Rhodobacteraceae or bacterium *Propionibacterium granulosum*.

30. The method of claim 12, wherein the physical condition is autonomic imbalance and the abundance proportion is an abundance proportion of bacteria belonging to family Oxalobacteraceae.

31. The method according to claim 12, wherein the physical condition is at least one of freckles of skin, dullness, sagging, wrinkles, and aged skin index.

\* \* \* \* \*